United States Patent
Lee

(10) Patent No.: US 10,519,512 B2
(45) Date of Patent: Dec. 31, 2019

(54) STK32C GENE RELEVANT TO BREAST CANCER AND USE THEREOF

(71) Applicant: DONGGUK UNIVERSITY INDUSTRY-ACADEMY COOPERATION FOUNDATION, Seoul (KR)

(72) Inventor: Chang-Hoon Lee, Gyeonggi-do (KR)

(73) Assignee: DONGGUK UNIVERSITY INDUSTRY-ACADEMIC COOPERATION FOUNDATION (KR)

(*) Notice: Subject to any disclaimer, the term of this patent is extended or adjusted under 35 U.S.C. 154(b) by 0 days.

(21) Appl. No.: 15/757,696

(22) PCT Filed: Aug. 19, 2016

(86) PCT No.: PCT/KR2016/009134
§ 371 (c)(1),
(2) Date: Mar. 6, 2018

(87) PCT Pub. No.: WO2017/043779
PCT Pub. Date: Mar. 16, 2017

(65) Prior Publication Data
US 2019/0169692 A1    Jun. 6, 2019

(30) Foreign Application Priority Data
Sep. 7, 2015 (KR) .................. 10-2015-0126560

(51) Int. Cl.
| | |
|---|---|
| C12N 15/113 | (2010.01) |
| C12Q 1/68 | (2018.01) |
| A61K 48/00 | (2006.01) |
| G01N 33/50 | (2006.01) |
| G01N 33/574 | (2006.01) |
| C12Q 1/6886 | (2018.01) |

(52) U.S. Cl.
CPC ............ *C12Q 1/6886* (2013.01); *A61K 48/00* (2013.01); *C12N 15/113* (2013.01); *G01N 33/50* (2013.01); *G01N 33/574* (2013.01); *C12Q 2600/106* (2013.01); *C12Q 2600/136* (2013.01); *C12Q 2600/158* (2013.01)

(58) Field of Classification Search
None
See application file for complete search history.

(56) References Cited

U.S. PATENT DOCUMENTS 8,859,202 B2    10/2014    Croce et al.

FOREIGN PATENT DOCUMENTS

| KR | 1020100104110 A | 9/2010 |
|---|---|---|
| WO | 2013/133675 A1 | 9/2013 |
| WO | 2014/191430 A1 | 4/2014 |

OTHER PUBLICATIONS

Lee et al., "Role of YANK3 in Breast Cancer," 2016, retrieved from https://www.snurips.ac.kr:444/cafe/seminar1/view_seminar_board.asp?s_idx=1514.

*Primary Examiner* — Tracy Vivlemore
(74) *Attorney, Agent, or Firm* — Riverside Law LLP

(57) ABSTRACT

The present invention relates to the serine threonine kinase 32C (STK32C) gene relevant to breast cancer and a use thereof, and particularly, to a composition for the diagnosis, prevention, or treatment of breast cancer using the STK32C gene. In the present invention, changes in breast cancer cells according to STK32C gene expression differences were identified, and a breast cancer inhibitory effect according to the inhibition of expression of the STK32C gene and YB-1, which is a substrate protein, were newly verified, and thus target therapies are expected in treatment of breast cancer through more fundamental approaches.

9 Claims, 39 Drawing Sheets
Specification includes a Sequence Listing.

FIG. 2-1
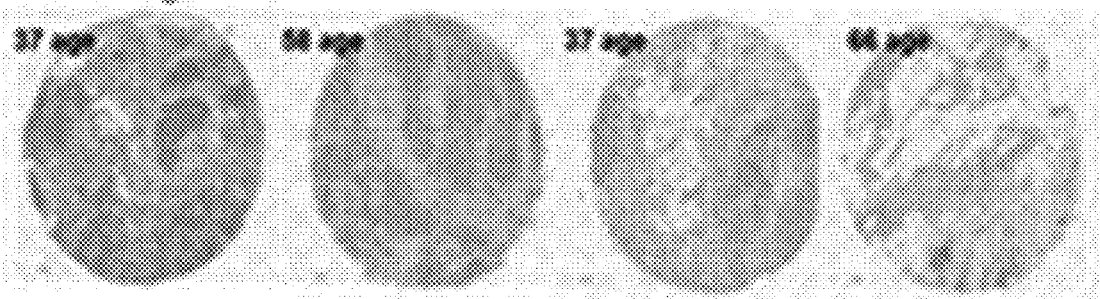
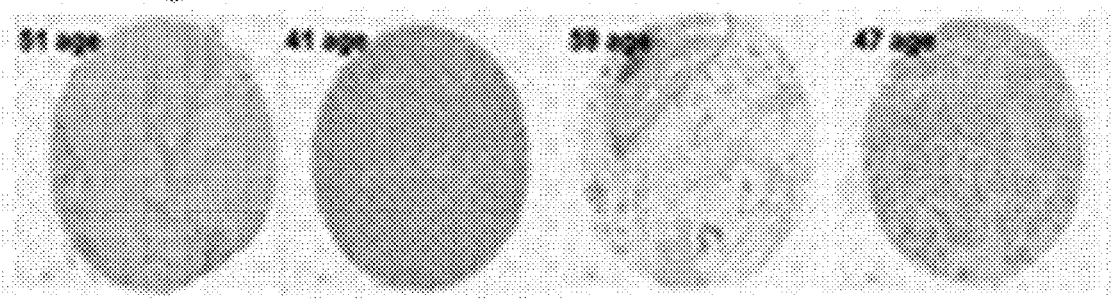
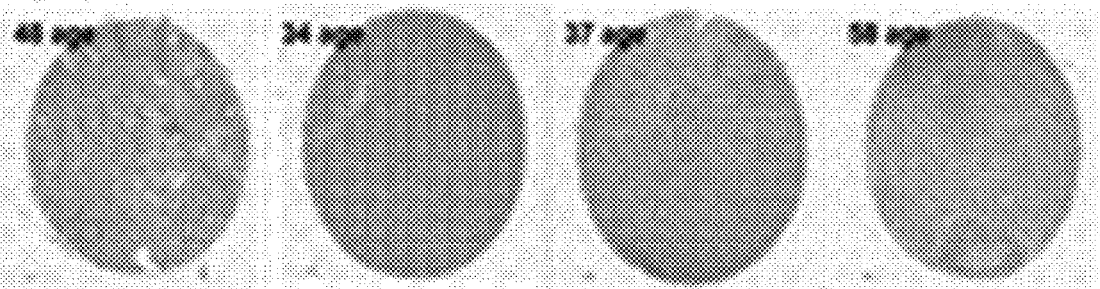
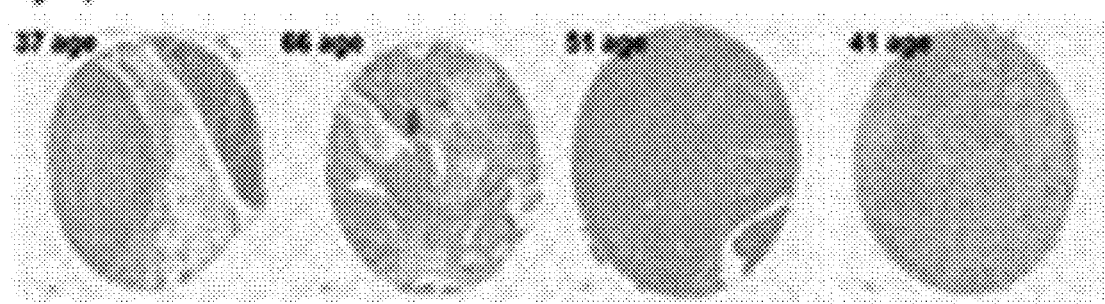

FIG. 2-2
Lymph node – metastatic carcinoma  Normal breast  Normal breast
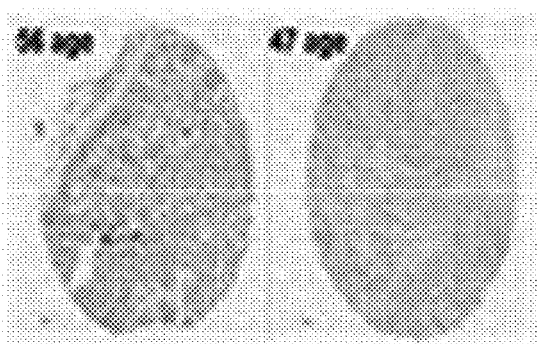
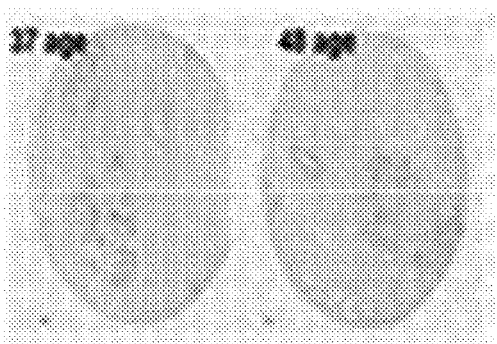
Normal breast
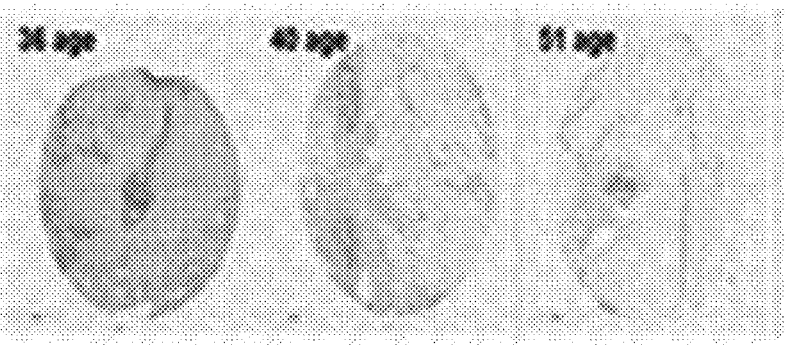
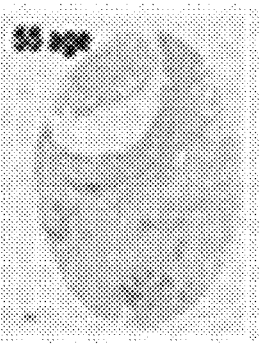
Normal breast
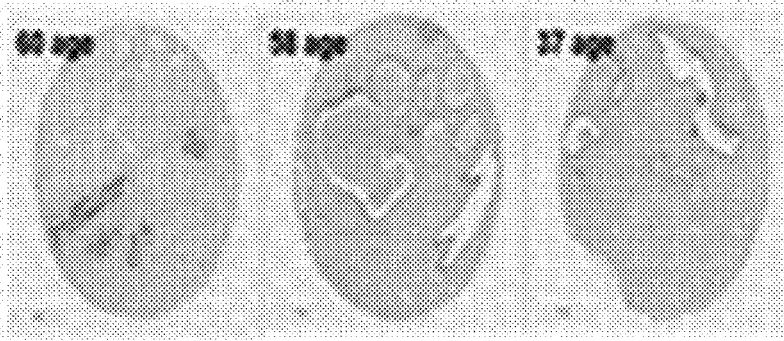

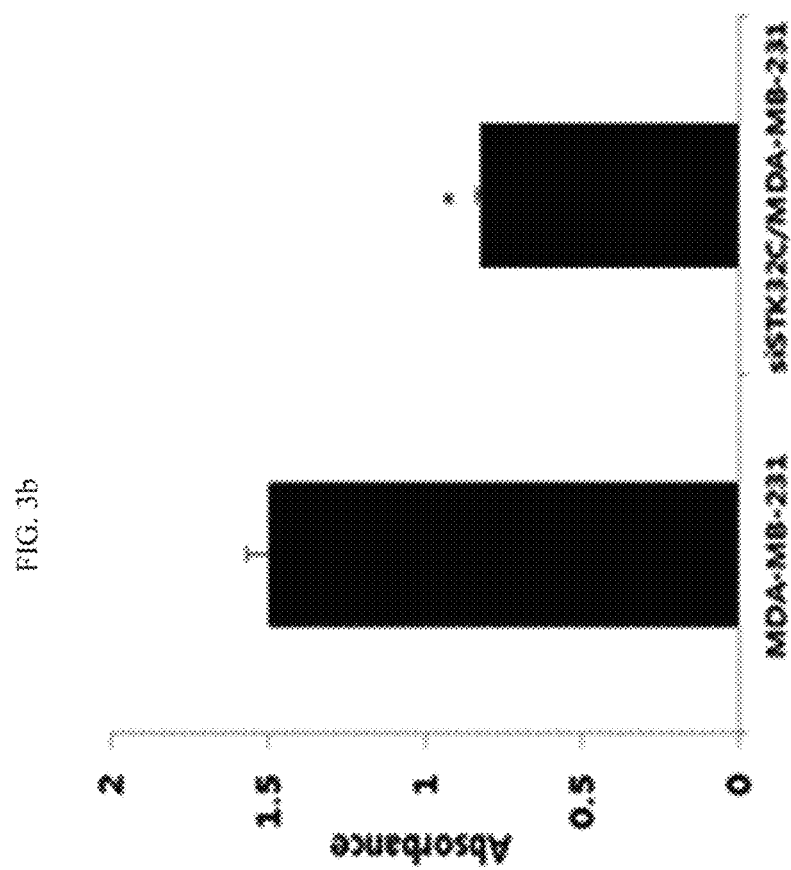

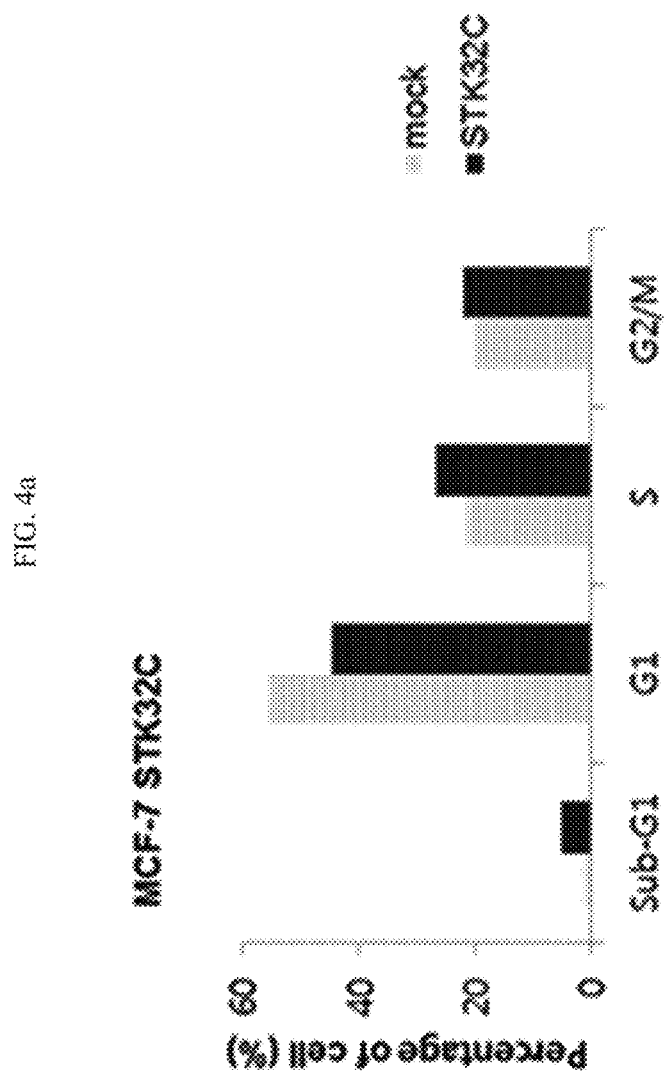

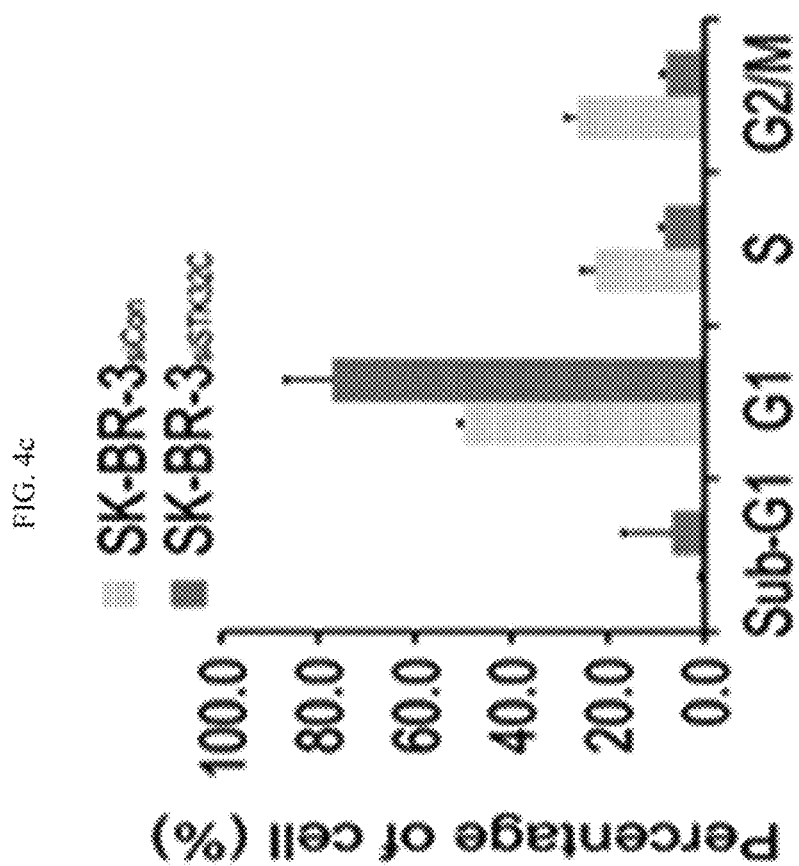

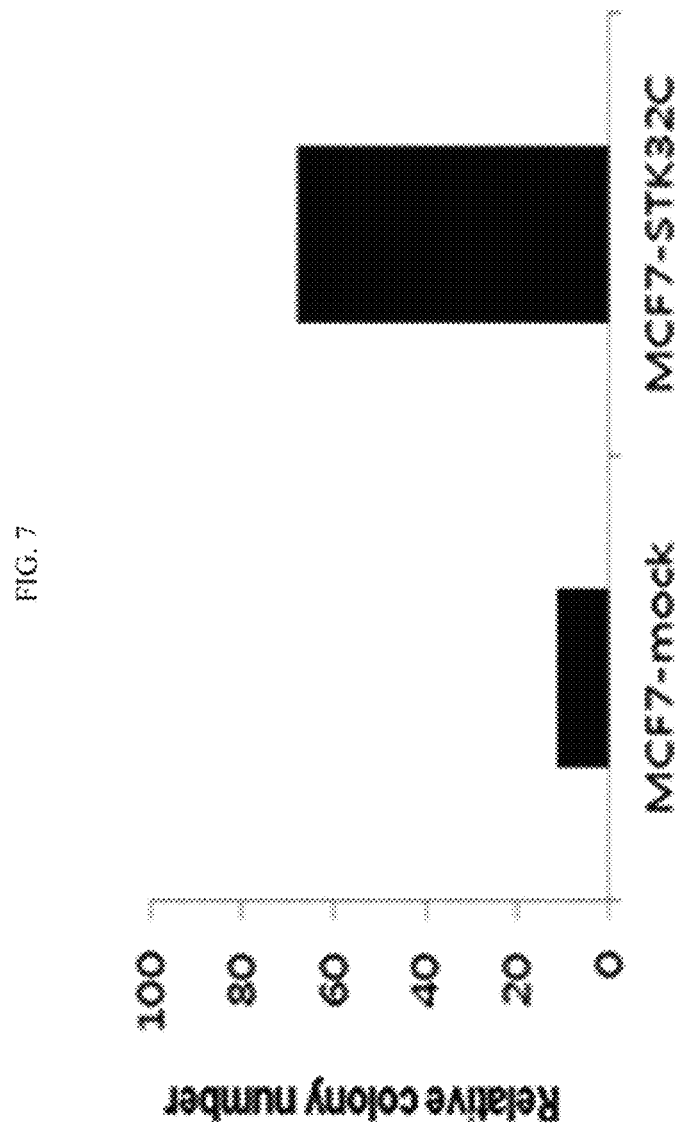

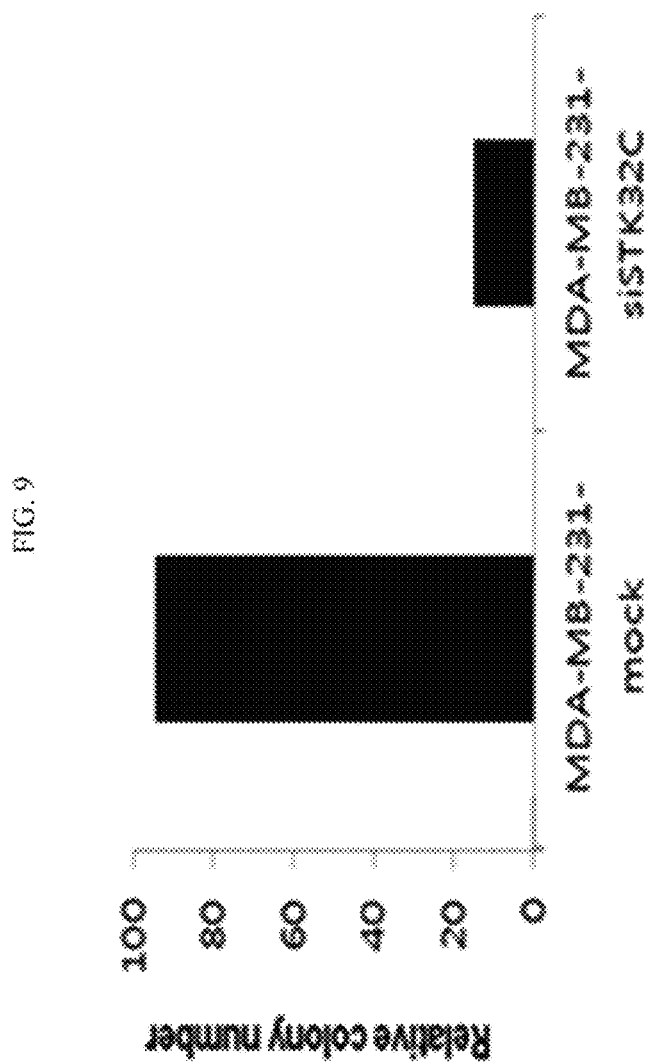

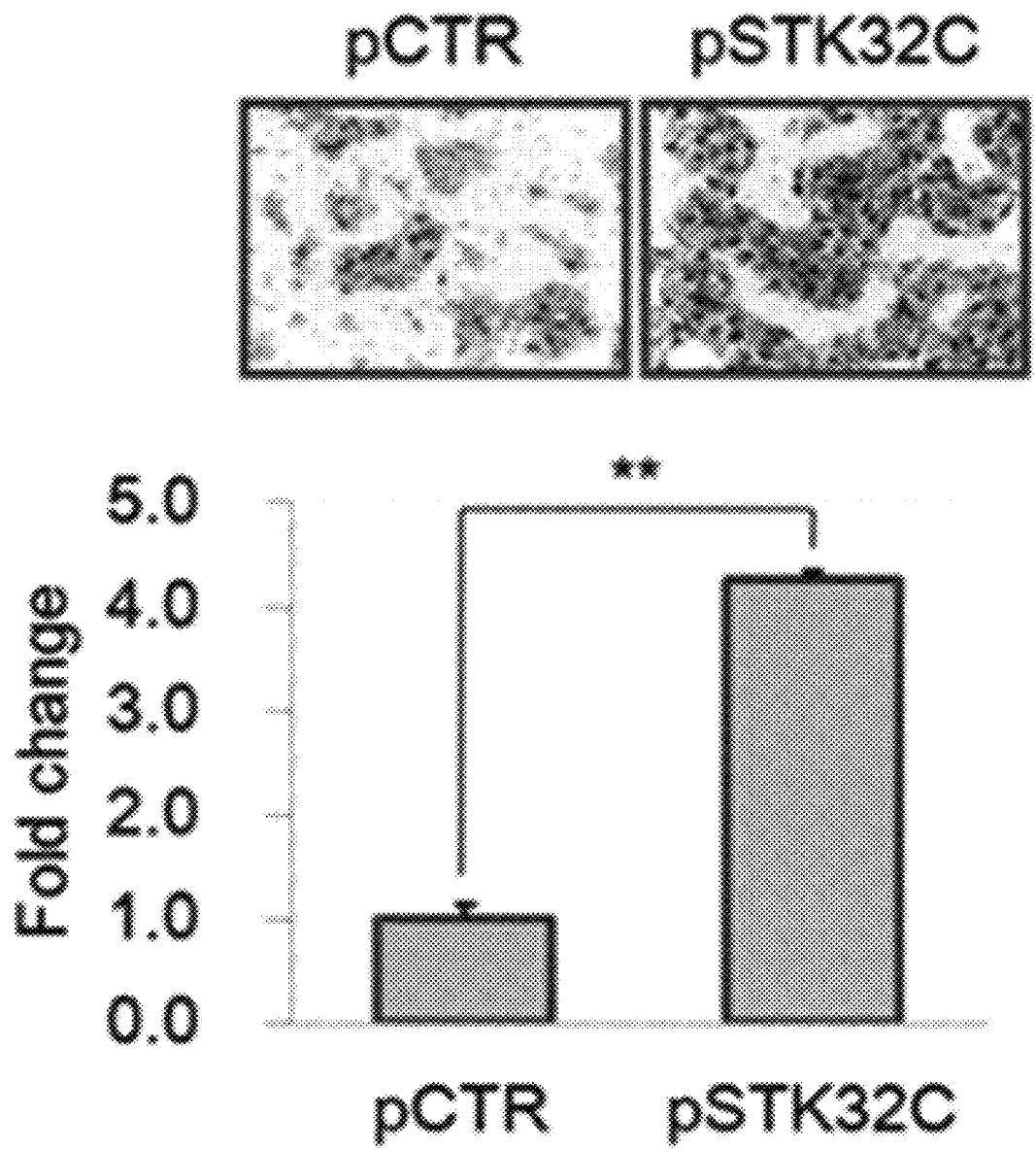

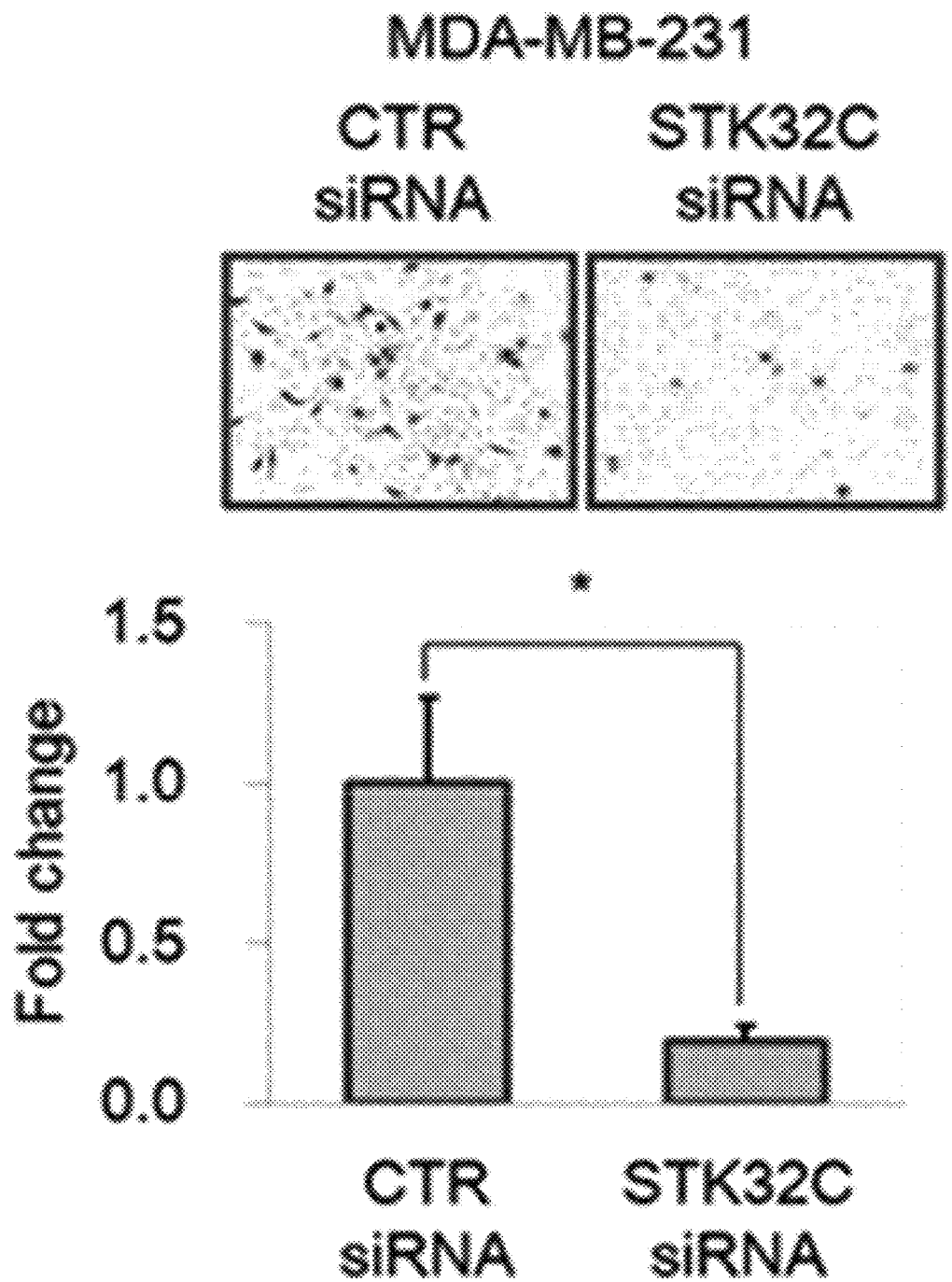

FIG. 13c
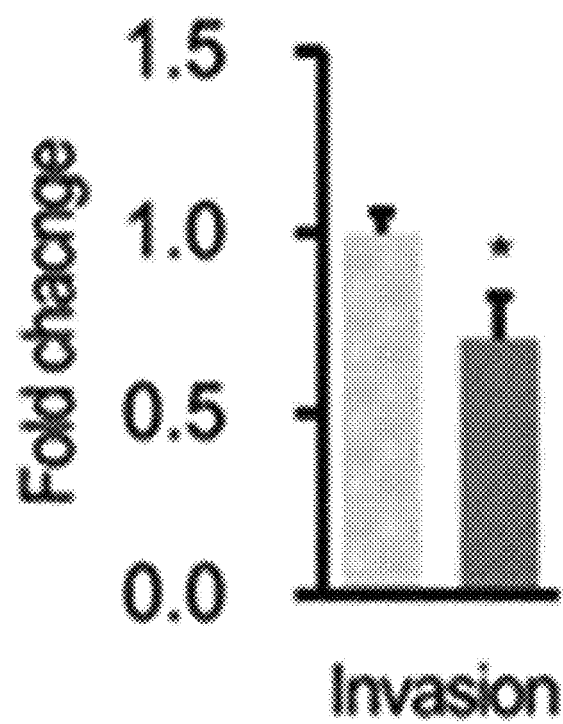

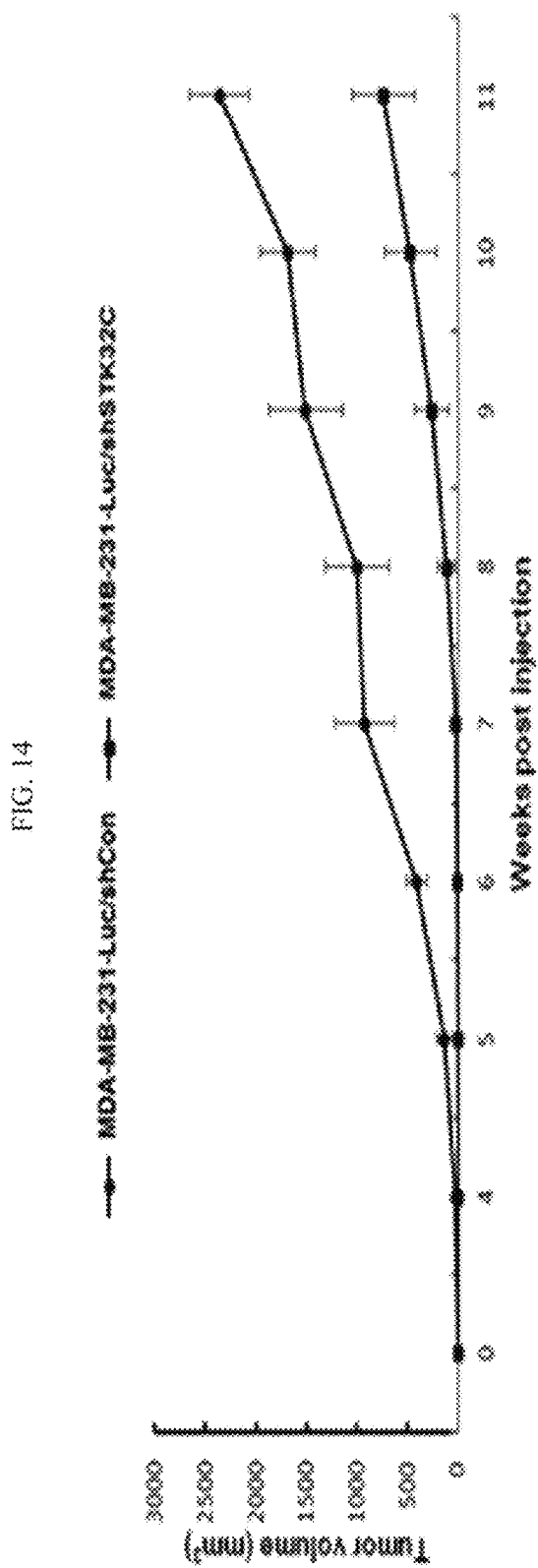

MDA-MB-231-Luc/shCon

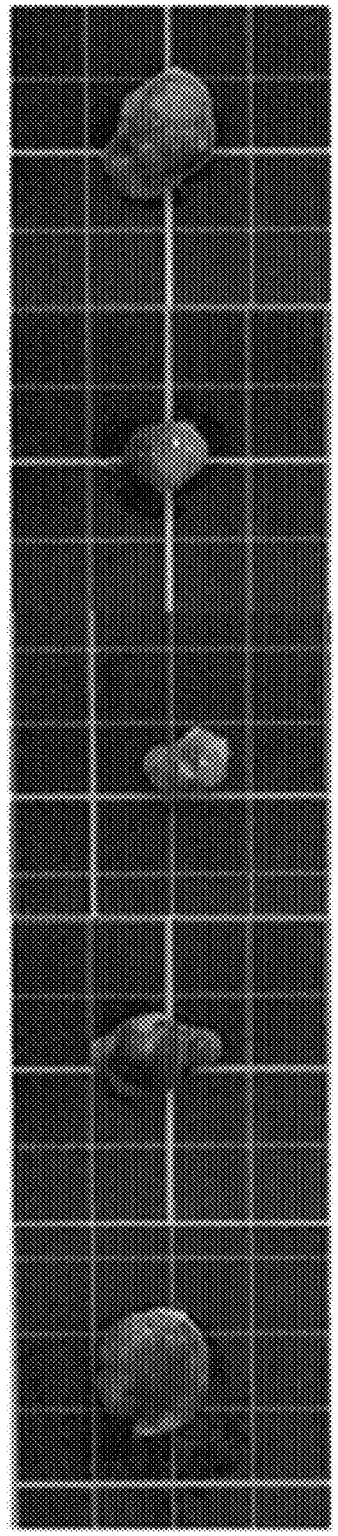

STK32C GENE RELEVANT TO BREAST CANCER AND USE THEREOF

STATEMENT REGARDING GOVERNMENT RIGHTS

The present invention was undertaken with the support of 1) Establishment of network regulating the stiffness of metastatic cancer cells No. 2014R1A2A1A01004016 grant funded by the National Research Foundation of Korea 2) Validation of novel target in new drug development for breast cancer No. 2017M3A9A8025606 grant funded by the National Research Foundation of Korea, and 3) Role of new targets regulating keratin reorganization in tumor microenvironment No. 2017R1A2A1A05000878 grant funded by the National Research Foundation of Korea.

CROSS-REFERENCE TO RELATED APPLICATIONS

This application is the U.S. national phase application filed under 35 U.S.C. § 371 claiming benefit to PCT International Application No. PCT/KR2016/009134, filed on Aug. 19, 2016, which claims priority to Korean Patent Application Serial No. 10-2015-0126560, filed on Sep. 7, 2015, the disclosure of which is incorporated herein by reference in its entirety.

TECHNICAL FIELD

The present invention relates to the serine threonine kinase 32C (STK32C) gene and a use thereof, and more particularly, to a composition for the diagnosis, prevention, or treatment of breast cancer using the STK32C gene.

BACKGROUND ART

The incidence of breast cancer in Korea is the fourth to fifth most common cancer among women in the 1990s, but most patients have been completely cured since 2001, and breast cancer is known to be the most severe cancer excluding thyroid cancer with a good prognosis. For example, according to age-standardized incidence rates of carcinomas in Korean female cancer patients, it can be confirmed that the incidence of breast cancer is most sharply increasing excluding thyroid cancer, the incidence of which is rapidly increasing due to the spread of diagnostic devices such as ultrasound. Therefore, there is a need to develop a method of accurately diagnosing and treating breast cancer.

Meanwhile, up to date, there are three main methods of treating cancer, which is a malignant tumor: invasive surgery, radiotherapy, and chemotherapy, and cancer is treated by one or a combination thereof. In particular, invasive surgery is a method of removing most of the diseased tissue, and such invasive surgery is inappropriate to treat tumors in sites that are difficult to remove or to treat disseminated tumors. In addition, radiotherapy is mainly used in acute inflammatory diseases, benign or malignant tumors, endocrine dysfunction, allergic diseases, and the like, and is generally effectively used for malignant tumors consisting of rapidly dividing cells. Such radiotherapy is disadvantageous in that radiotherapy may weaken or lose the function of normal tissues and may cause skin diseases in treated sites after the therapy, and, in particular, may cause severe side effects such as delayed intelligence development or bone developmental disorders in the case of children with developing organs. In addition, chemotherapy is widely used to treat breast cancer, lung cancer, and testicular cancer by disturbing the replication or metabolism of cancer cells, and such a method is most disadvantageous in that there are side effects induced by systemic chemotherapy used in cancer treatment. The side effects by chemotherapy may have a significant effect on patients' lives and increase patients' anxieties about treatment. In addition, a side effect associated with chemotherapeutic agents is dose limiting toxicity (DLT), which should be generally taken into account when administering these drugs. For example, mucositis is DLT for various anticancer drugs (5-fluorouracil and methotrexate, which are antimetabolite cytotoxic agents, and doxorubicin which is an antitumor antibiotic). Among these chemotherapy side effects, the most severe cases require hospitalization or painkillers for the treatment of pain. As such, side effects due to chemotherapy and radiotherapy have become an important issue in the treatment of cancer patients.

Thus, as an alternative to addressing the above-described problems of conventional cancer therapeutics, cancer-related gene targeting treatment has attracted much attention. In particular, breast cancer gene 1 (BRCA1), breast cancer gene 2 (BRCA2), and the like have been reported as genes associated with the onset of breast cancer, and research thereon has been actively conducted (see Korean Patent Application Publication No. 10-2013-0057760), but results thereof are insufficient.

DISCLOSURE

Technical Problem

The present invention has been made in view of the above problems, and the inventors of the present invention verified a breast cancer inhibitory effect by the inhibition of expression of the serine threonine kinase 32C (STK32C) gene, thus completing the present invention based on the above finding.

Therefore, an object of the present invention is to provide a pharmaceutical composition for preventing or treating breast cancer, which includes, as an active ingredient, an expression or activity inhibitor of serine threonine kinase 32C (STK32C).

In addition, another object of the present invention is to provide a composition for diagnosing breast cancer, which includes an agent that measures an expression or activity level of STK32C.

In addition, still another object of the present invention is to provide a method of screening a breast cancer therapeutic material, including: a) treating STK32C-expressing cells with a test material; b) measuring an expression or activity degree of STK32C in the cells; and c) selecting a test material that inhibits the expression or activity of STK32C when compared to a control not treated with the test material, as a breast cancer therapeutic material.

In addition, yet another object of the present invention is to provide a method of providing information on a breast cancer diagnosis, including: a) measuring an expression or activity degree of STK32C in a subject-derived biological sample; and b) predicting or diagnosing a case in which the measured expression or activity degree of STK32C is higher than that of a normal control, as having breast cancer.

However, technical problems to be achieved by the present invention are not limited to the above-described technical problems, and other unmentioned technical problems will become apparent from the following description to those of ordinary skill in the art.

Technical Solution

To achieve the above-described objects of the present invention, the present invention provides a pharmaceutical composition for preventing or treating breast cancer, which includes, as an active ingredient, an expression or activity inhibitor of serine threonine kinase 32C (STK32C).

In one embodiment of the present invention, the expression inhibitor of STK32C may include at least one selected from the group consisting of an antisense oligonucleotide, siRNA, shRNA, microRNA, and a ribozyme that specifically bind to STK32C.

In another embodiment of the present invention, the activity inhibitor of STK32 may include at least one selected from the group consisting of a compound, a peptide, a protein, an aptamer, and an antibody that specifically bind to STK32C.

In another embodiment of the present invention, the composition may inhibit the phosphorylation of YB-1.

The present invention provides a composition for diagnosing breast cancer, which includes an agent that measures an expression or activity level of STK32C.

In one embodiment of the present invention, the agent that measures an expression or activity level of STK32C may include at least one selected from the group consisting of a primer, a probe, and an antibody that specifically bind to STK32C.

The present invention provides a method of screening a breast cancer therapeutic material, including: a) treating STK32C-expressing cells with a test material; b) measuring an expression or activity degree of STK32C in the cells; and c) selecting a test material that inhibits the expression or activity of STK32C when compared to a control not treated with the test material, as a breast cancer therapeutic material.

In one embodiment of the present invention, the STK32C-expressing cells may be selected from the group consisting of MCF-10A, MCF-7, MDA-MB-231, and SK-BR-3 breast cancer cells.

In another embodiment of the present invention, the measuring of the expression or activity degree of STK32C may be performed by measuring a phosphorylation degree of YB-1 by STK32C.

The present invention provides a method of providing information on a breast cancer diagnosis, including: a) measuring an expression or activity degree of STK32C in a subject-derived biological sample; and b) predicting or diagnosing a case in which the measured expression or activity level of STK32C is higher than that of a normal control, as having breast cancer.

The present invention provides a method of treating breast cancer, including administering the expression or activity inhibitor of STK32C to an individual.

The present invention provides a use of an expression or activity inhibitor of STK32C for preparing a breast cancer therapeutic agent.

Advantageous Effects

The present invention relates to the serine threonine kinase 32C (STK32C) gene associated with breast cancer and a use thereof, and a high expression level of the STK32C gene was verified in a variety of breast cancer cells or tissues, and changes in breast cancer cells according to STK32C gene expression differences were experimentally verified. In addition, a breast cancer inhibitory effect by the inhibition of expression of the STK32C gene and YB-1, which is a substrate protein, were newly identified, and thus the STK32C gene is expected to be used as a target gene for the diagnosis or treatment of breast cancer.

DESCRIPTION OF DRAWINGS

FIG. 3b illustrates results of a change in the proliferative ability of MDA-MB-231 cells (siSTK32C/MDA-MB-231) in which the expression of the STK32C gene was inhibited.

FIG. 4a illustrates results of cell cycle changes in MCF-7 cells (STK32C) in which the STK32C gene was overexpressed.

FIG. 4c illustrates results of cell cycle changes in SK-BR-3 cells (siSTK32C) in which the expression of the STK32C gene was inhibited.

FIG. 7 illustrates results of the comparison between the number of colonies in MCF-7 cells as a control (MCF7-mock) and the number of colonies in MCF-7 cells (MCF7-STK32C) in which the STK32C gene was overexpressed.

FIG. 9 illustrates results of the comparison between the number of colonies in MDA-MB-231 cells as a control (MDA-MB-231-mock) and the number of colonies in MCF-7 cells (MDA-MB-231-siSTK32C).

FIG. 12a illustrates verification results of the migration of cancer cells in MCF-10 cells (pSTK32C) in which the STK32C gene was overexpressed.

FIG. 12b illustrates verification results of the migration of cancer cells in MDA-MB-231 cells (STK32C siRNA) in which the expression of the STK32C gene was inhibited.

FIG. 13c illustrates verification results of the invasiveness of cancer cells in SK-BR-3 cells (STK32C siRNA) in which the expression of the STK32C gene was inhibited.

FIG. 14 illustrates results showing changes in the volume of cancer tissue over time in a mouse animal model (MDA-MB-231-luc/shSTK32C) into which a MDA-MB-231 cell line, in which the expression of the STK32C gene was inhibited, was injected.

FIG. 15b illustrates visual observation results of changes in the volume of cancer tissue in a mouse animal model (MDA-MB-231-luc/shSTK32C) into which a MDA-MB-231 cell line, in which the expression of the STK32C gene was inhibited, was injected.

BEST MODE

Figure 1:
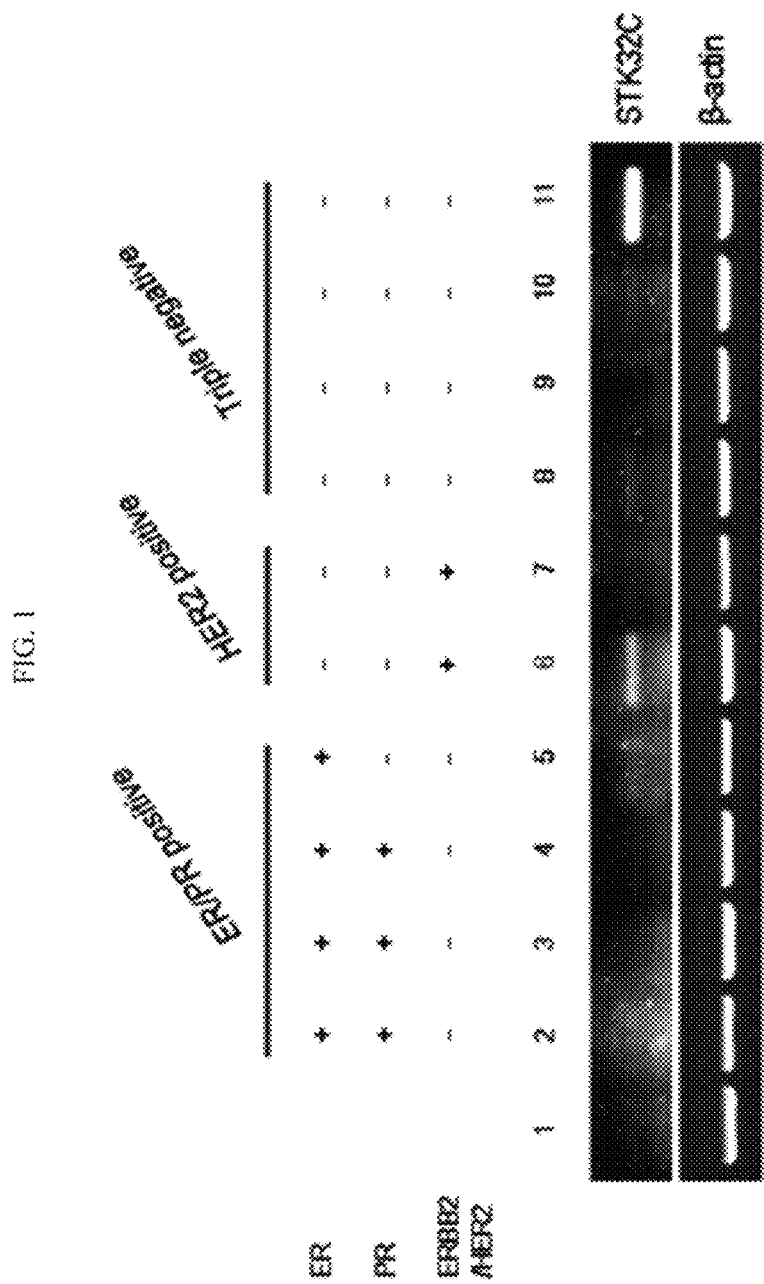
FIG. 1 illustrates verification results of the expression of the STK32C gene by reverse transcription polymerase chain reaction (RT-PCR) in ER/PR positive, HER2 positive, and Triple negative (ER/PR/HER2 negative) breast cancer cells.

The inventors of the present invention identified high expression levels of the serine threonine kinase 32C (STK32C) gene in a variety of breast cancer cells or tissues, and confirmed changes in proliferation, cell cycle, colony formation, epithelial to mesenchymal transition, and invasiveness of breast cancer cells according to STK32C gene expression differences. In addition, the inventors verified a breast cancer inhibitory effect by the inhibition of expression of the STK32C gene in a mouse animal model, thus completing the present invention based on the above findings.

Hereinafter, the present invention will be described in detail.

The present invention provides a pharmaceutical composition for the prevention or treatment of breast cancer, which includes an expression or activity inhibitor of STK32C as an active ingredient.

The term "prevention" as used herein means all actions that inhibit breast cancer or delay the onset thereof via administration of the pharmaceutical composition according to the present invention.

The term "treatment" as used herein means all actions that alleviate or beneficially change symptoms due to breast cancer via administration of the pharmaceutical composition according to the present invention.

Breast cancer, which is a disease to be prevented or treated by the composition of the present invention, is a tumor consisting of cancer cells occurring in the breast, and generally refers to cancer occurring in milk ducts and lobules of the breast. The basic treatment of breast cancer is surgical resection of the lesion, and it is necessary for all patients to undergo a surgical resection unless there is metastasis to other organs. In addition, anticancer chemotherapy, radiotherapy, anti-hormonal therapy, and the like are required as adjuvant therapies, and the composition of the present invention is provided as a breast cancer therapeutic agent targeting STK32C as gene targeting treatment.

In the present invention, although the serine/threonine kinase 32C (STK32C) gene, which is a target gene for breast cancer treatment, is one of the serine/threonine protein kinases, and is known to be associated with sweet taste signaling, breast cancer treatment through the inhibition of STK32C expression or activity has never been reported.

In the present invention, the expression inhibitor of STK32C may include at least one selected from the group consisting of an antisense oligonucleotide, siRNA, shRNA, microRNA, and a ribozyme that specifically bind to STK32C, and the activity inhibitor of STK32C may include at least one selected from the group consisting of a compound, a peptide, a protein, an aptamer, and an antibody that specifically bind to STK32C, but the expression or activity inhibitor of STK32C may include any preparations without limitation as long as they can inhibit the expression or activity of the STK32C gene.

The pharmaceutical composition according to the present invention may include a pharmaceutically acceptable carrier, in addition to the active ingredient. The pharmaceutically acceptable carrier, which is commonly used in formulation, includes lactose, dextrose, sucrose, sorbitol, mannitol, starch, acacia gum, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and mineral oil, but the present invention is not limited to the above examples. The pharmaceutical composition may further include, in addition to the above-described components, a lubricant, a wetting agent, a sweetener, a flavor enhancer, an emulsifying agent, a suspension agent, a preservative, or the like.

The pharmaceutical composition of the present invention may be administered orally or parenterally (e.g., intravenously, subcutaneously, intraperitoneally, or locally) according to desired method, and a suitable dose thereof may vary depending on conditions and body weights of patients, the severity of disease, types of drugs, administration route, and administration time, but may be appropriately selected by those of ordinary skill in the art.

The pharmaceutical composition of the present invention is administered in a pharmaceutically effective amount. The term "pharmaceutically effective amount" as used herein refers to an amount sufficient to treat diseases at a reasonable benefit/risk ratio applicable to medical treatment, and an effective dosage level may be determined according to factors including type of diseases of patients, the severity of disease, the activity of drugs, sensitivity to drugs, administration time, administration routes, excretion rate, treatment periods, and simultaneously used drugs, and other factors well known in the medical field. The pharmaceutical composition according to the present invention may be administered as an individual therapeutic agent or in combination with other therapeutic agents, may be administered consecutively or simultaneously with existing therapeutic agents, and may be administered in a single dose or multiple doses. It is important to administer the pharmaceutical composition in the minimum amount that enables achievement of the maximum effects without side effects in consideration of all the above-described factors, and this may be easily determined by those of ordinary skill in the art.

In particular, the effective amount of the pharmaceutical composition of the present invention may vary according to the age, gender, condition, and body weight of a patient, the absorption of an active ingredient in the body, inactivity rate, excretion rate, the type of diseases, and drugs used along therewith, and the pharmaceutical composition may be administered generally in a dose of 0.001 mg/kg to 150 mg/kg, preferably, 0.01 mg/kg to 100 mg/kg daily or every other day, or may be administered once to three times. However, the effective amount may be increased or decreased according to administration route, the severity of obesity, gender, body weight, age, and the like, and thus is not intended to limit the scope of the present invention in any way.

According to another embodiment of the present invention, the present invention provides a method of treating breast cancer, including administering the pharmaceutical composition to an individual. The term "individual" as used herein refers to a subject with a disease requiring treatment and, more particularly, includes mammals such as humans or non-human primates, e.g., mice, rats, dogs, cats, horses, cows, and the like.

According to another embodiment of the present invention, the present invention provides a composition for the diagnosis of breast cancer, which includes an agent that measures an expression or activity level of serine threonine kinase 32C (STK32C).

The term "diagnosis" as used herein means actions that identify pathological conditions, i.e., the existence or characteristics of breast cancer, via administration of the composition according to the present invention.

In the present invention, the agent for measuring an expression or activity level of STK32C may include at least one selected from the group consisting of a primer, a probe, a protein, and an antibody that specifically bind to STK32C, but may include any agent without limitation as long as it is an agent capable of measuring an expression or activity level of the STK32C gene.

In one embodiment of the present invention, high expression levels of the STK32C gene were identified in a variety of breast cancer cells and tissues, from which it was confirmed that the onset of breast cancer was closely related to the STK32C gene (see Example 1), and, based on this result, it was confirmed that, as the STK32C gene was overexpressed, proliferation, cell cycle, colony formation, epithelial to mesenchymal transition, and invasiveness of breast cancer cells were accelerated, whereas, as the STK32C gene was inhibited, a tendency opposite to the above tendency was shown (see Example 2). In addition, an effect of the STK32C gene on inhibiting breast cancer by the inhibition thereof was verified using a mouse animal model (see Example 3), the YB-1 protein was verified as a substrate of the STK32C gene, from which it was particularly confirmed that breast cancer could be treated by controlling the expression or activity of the STK32C gene (see Example 4).

Thus, as another embodiment of the present invention, the present invention provides a method of screening a breast cancer therapeutic material, including: a) culturing STK32C-expressing cells with or without a test material; b) measuring an expression or activity degree of STK32C in the cells; and c) selecting a test material that inhibits the expression or activity of STK32C when compared to a group of the STK32C-expressing cells cultured without the test material, as a breast cancer therapeutic material.

In the present invention, the STK32C-expressing cells may be selected from the group consisting of MCF-10A, MCF-7, and MDA-MB-231 breast cancer cells, but may include any breast cancer cells without limitation as long as they are cells capable of identifying changes in expression of the STK32C gene.

In the present invention, the measuring of the expression or activity degree of STK32C may be performed using one or more methods selected from the group consisting of polymerase chain reaction (PCR), reverse transcription PCR (RT-PCR), competitive RT-PCR, real-time RT-PCR, RNase protection assay (RPA), northern blotting, DNA chips, western blotting, enzyme-linked immunosorbent assay (ELISA), radioimmunoassay (RIA), radioimmunodiffusion, Ouchterlony immunodiffusion, rocket immunoelectrophoresis, immunoprecipitation assay, complement fixation assay, protein chips, and in vitro kinase assay, and, preferably, may be measured through a phosphorylation degree of YB-1 by STK32C, but the present invention is not limited to the above examples.

As another embodiment of the present invention, the present invention provides a method of providing information on a breast cancer diagnosis, including: a) measuring an expression or activity degree of STK32C in a subject-derived biological sample; and b) predicting or diagnosing a case in which the measured expression or activity degree of STK32C is higher than that of a normal control, as having breast cancer.

In the present invention, the biological sample includes samples of blood and other liquids of biological origin, biopsy specimens, and solid tissue samples such as tissue culture or cells derived therefrom. More particularly, the biological sample may include tissues, extracts, cell lysates, whole blood, plasma, serum, saliva, ocular humor, cerebrospinal fluids, sweat, urine, breast milk, ascitic fluid, synovia, peritoneal fluid, and the like, and the sample may be collected from an animal, preferably, a mammal, and, most preferably, a human.

The sample may be pretreated prior to use in detection, and examples thereof include filtration, distillation, extraction, enrichment, inactivation of interfering components, the addition of a reagent, and the like. In addition, nucleic acids and proteins may be isolated from the sample to be used in detection.

Hereinafter, exemplary embodiments will be described to aid in understanding of the present invention. However, the following examples are provided only to more easily understand the present invention and are not intended to limit the content of the present invention.

Example 1. Verification of Expression of STK32C in Breast Cancer Cells or Tissues In the present example, to verify the relationship between the onset of breast cancer and the serine threonine kinase 32C (STK32C) gene of SEQ ID NO: 1, the expression of the STK32C gene was identified in various breast cancer cells or tissues. In particular, it was examined whether the STK32C gene was expressed or not in ER/PR positive, HER2 positive, and Triple negative (ER/PR/HER2 negative) breast cancer cells through RT-PCR using STK32C primers.

As a result, as illustrated in FIG. 1, the expression of the STK32C gene was verified in ER/PR positive, HER2 positive, and Triple negative (ER/PR/HER2 negative) breast cancer cells.

In addition, STK32C gene expression patterns in various breast cancer tissues such as infiltrating duct carcinoma, metastatic carcinoma, sarcomas, intraductal papillary carcinoma, atypical medullary carcinoma, and metaplastic carcinoma were compared with those in normal mammary tissue through breast cancer tissue arrays.

Figures 2, 3:
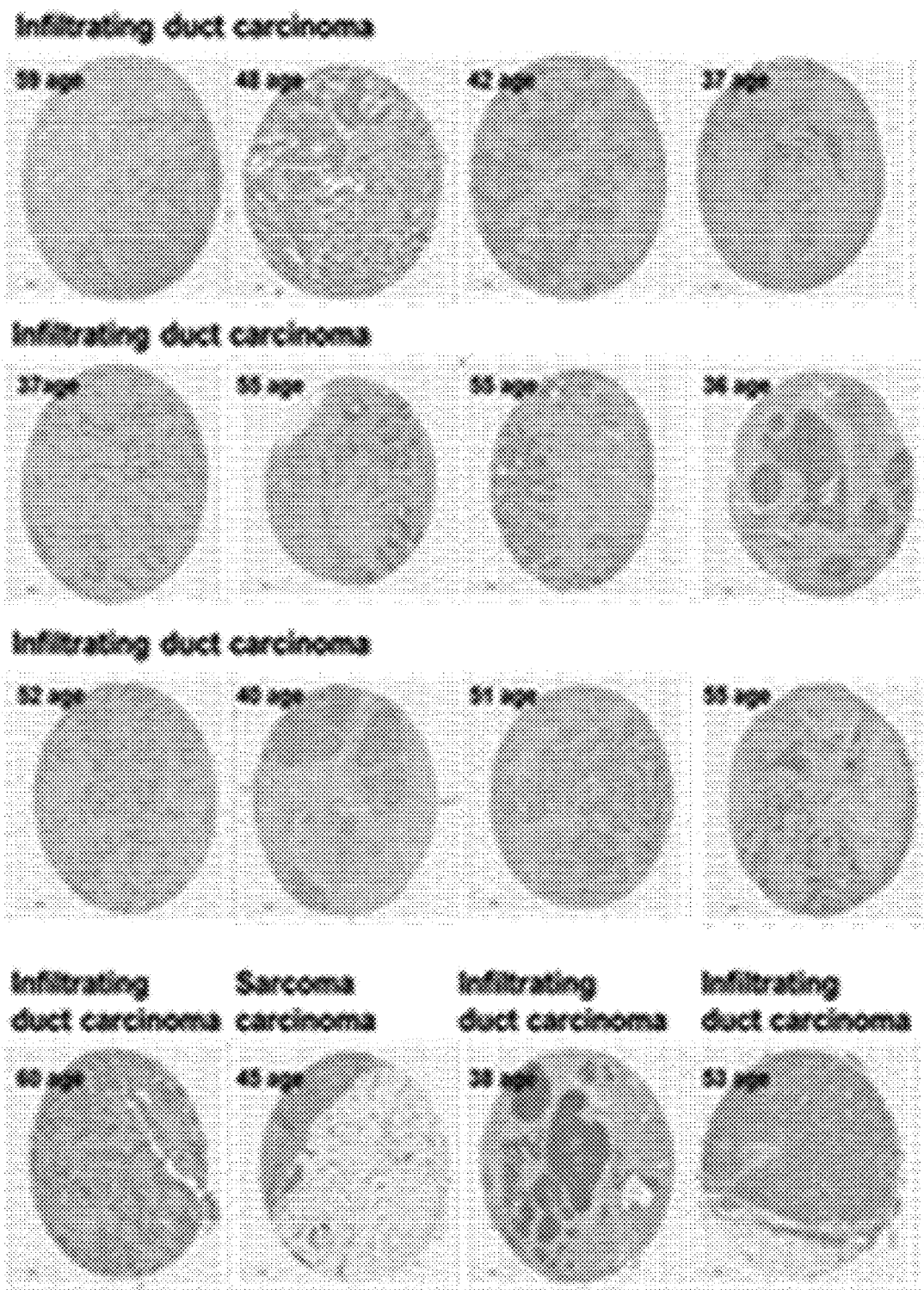
FIG. 2 illustrates verification results of the expression of the STK32C gene through a breast cancer tissue array in a variety of breast cancer tissues.

As a result, as illustrated in FIG. 2, the expression of the STK32C gene was low in normal mammary tissue (normal breast), whereas the expression of the STK32C gene was high in the various breast cancer tissues, and, in particular, the expression of the STK32C was observed as being higher in infiltrating ductal carcinoma.

Taken together, the above results indicate that the onset of breast cancer is closely associated with the STK32C gene.

Example 2. Verification of Changes of Breast Cancer Cells According to STK32C Expression In the present example, the effect of the STK32C gene on breast cancer cells was examined and identified. Thus, changes in proliferation, cell cycle, colony formation, epithelial to mesenchymal transition, and invasiveness of breast cancer cells were identified according to the increase or inhibition of expression of the STK32C gene.

Example 2-1. Verification of Effect on Proliferation of Breast Cancer Cells

Changes in proliferative ability of breast cancer cells according to the expression of the STK32 gene were identified using MCF-7 cells and MDA-MB-231 cells, showing differences in the expression of the STK32C gene. In particular, the STK32C gene was overexpressed in the MCF-7 cells showing a relatively low expression level of the STK32C gene, whereas the STK32C gene was subjected to gene silencing in the MDA-MB-231 cells showing a relatively high expression level of the STK32C gene. The gene silencing was performed using siRNAs shown in Table 1 below.

TABLE 1

| siRNA | | Nucleotide sequences |
|---|---|---|
| sc-90587A | Sense | GAUGUCAAGCCUGACAACAtt (SEQ ID NO: 1) |
| | Antisense | UGUUGUCAGGCUUGACAUCtt (SEQ ID NO: 2) |
| sc-90587B | Sense | CCGAGAAUGACUAUCUUCAtt (SEQ ID NO: 3) |
| | Antisense | UGAAGAUAGUCAUUCUCGGtt (SEQ ID NO: 4) |

Subsequently, the proliferative abilities of the breast cancer cells were compared by measuring absorbance of each case, and MCF-7 and MDA-MB-231 cells prior to overexpression or inhibition of the STK32C gene were used as controls.

Figure 3A:
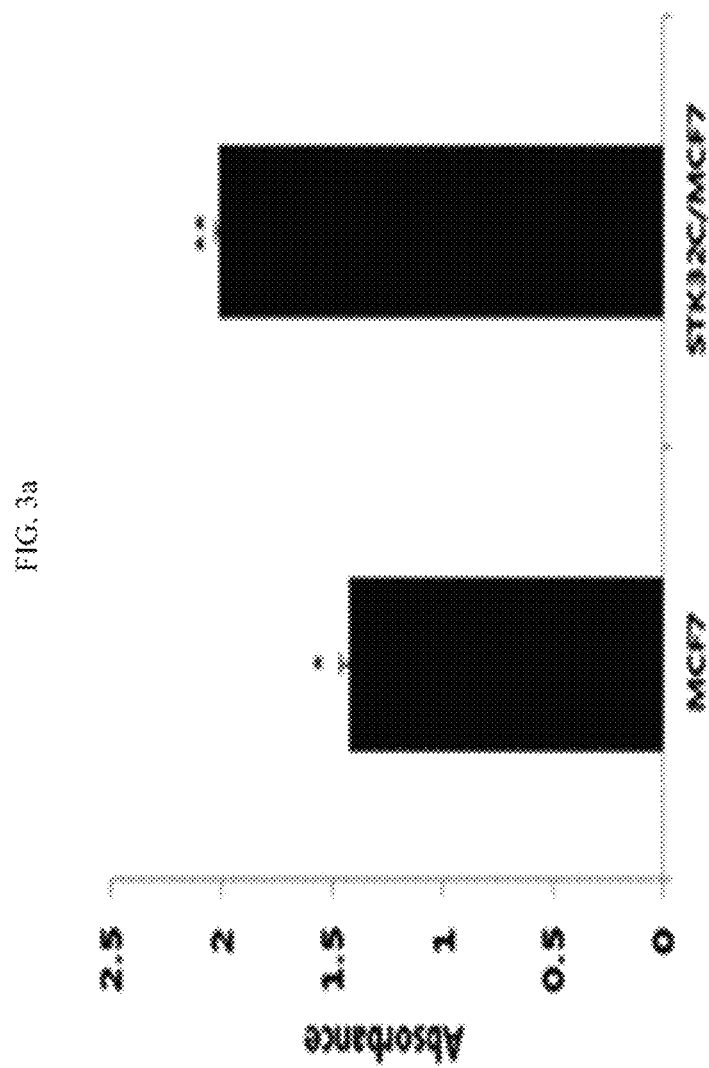
FIG. 3a illustrates results of a change in the proliferative ability of MCF-7 cells (STK32C/MCF7) in which the STK32C gene was overexpressed.
Figure 3C:
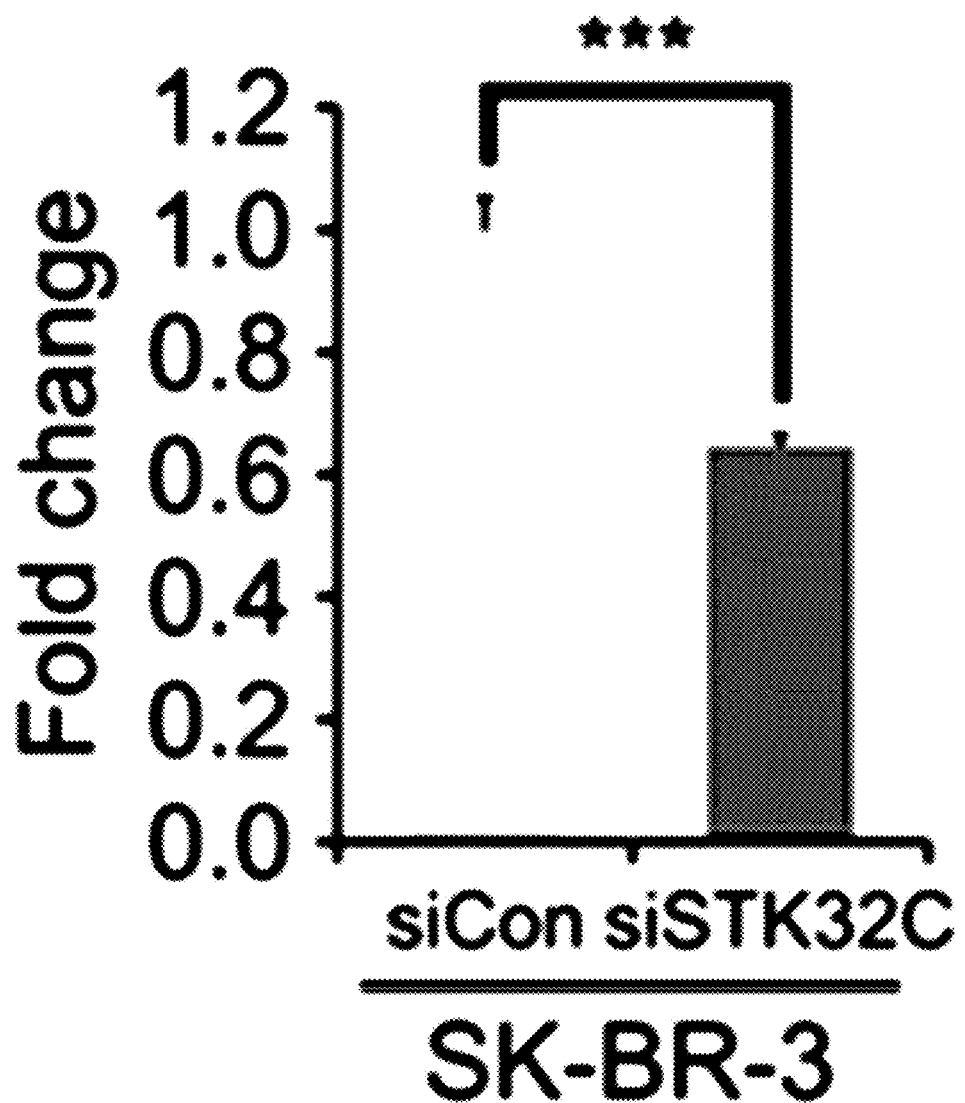
FIG. 3c illustrates results of a change in the proliferative ability of SK-BR-3 cells (siSTK32C/SK-BR-3) in which the expression of the STK32C gene was inhibited.

As a result, as illustrated in FIG. 3, it was confirmed that the proliferation of breast cancer cells was increased in MCF-7 cells (STK32C/MCF7) in which the STK32C gene was overexpressed, as compared to the control (see FIG. 3a), whereas the proliferation of breast cancer cells was decreased in MDA-MB-231 cells and SK-BR-3 cells (siSTK32C/MDA-MB-231), in which the expression of the STK32C gene was inhibited (see FIGS. 3b and 3c). These results indicate that the proliferation of breast cancer cells is accelerated by overexpression of the STK32C gene and is inhibited by the inhibition of STK32C gene expression.

Example 2-2. Verification of Effect on Cell Cycle of Breast Cancer Cells

Unlike normal cells, cancer cells lose regulatory action on cell division and thus continuously repeat only phases of the cell cycle associated with division and proliferation, and thus, in the present example, changes in the cell cycle according to STK32C gene expression differences were examined. In particular, the STK32C genes of MCF-7 cells and MDA-MB-231 cells were overexpressed or inhibited using the same method as that used in Example 2-1 above, and then the distribution of each phase of the cell cycle (Sub-G1, G1, S, and G2/M) was quantified for comparison. As controls, MCF-7 cells and MDA-MB-231 cells, prior to the overexpression or inhibition of the STK32C gene, were used.

Figures 2, 3, 4:
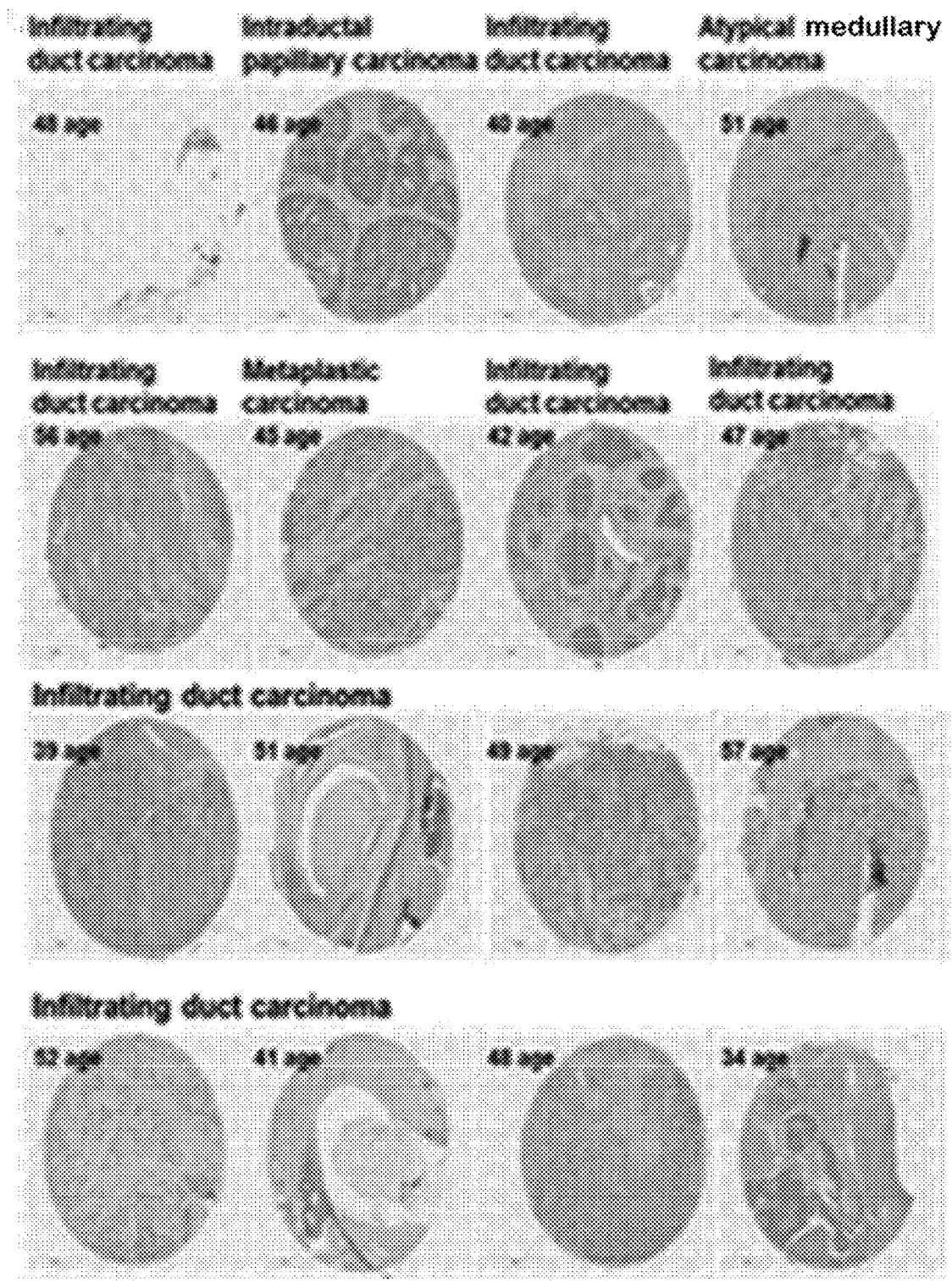
Figure 4B:
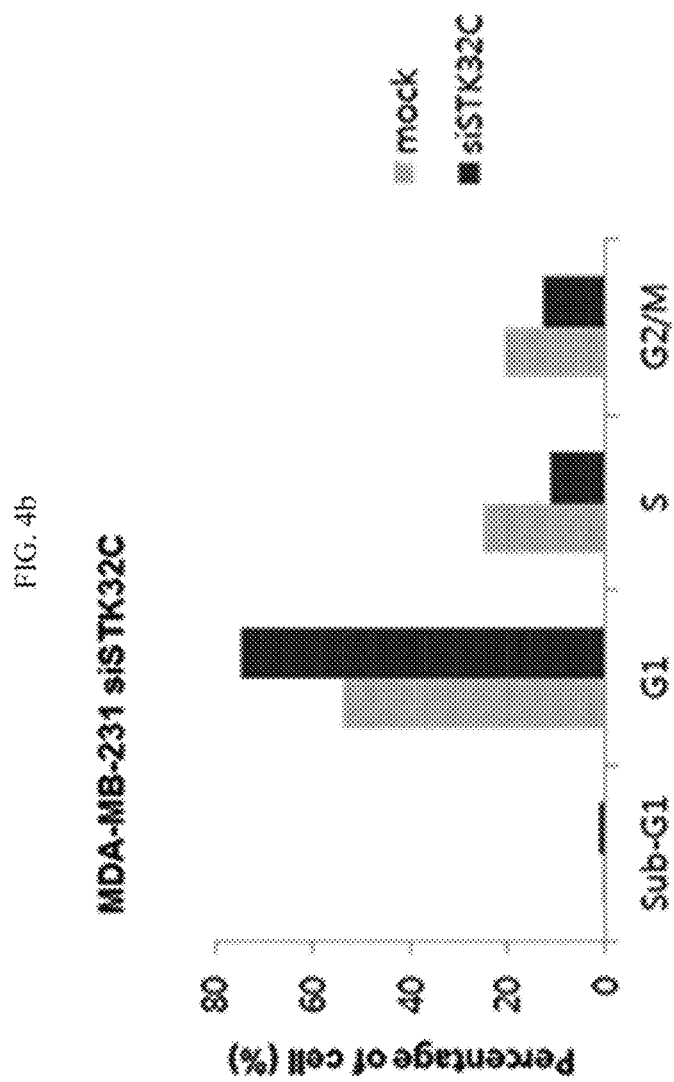
FIG. 4b illustrates results of cell cycle changes in MDA-MB-231 cells (siSTK32C) in which the expression of the STK32C gene was inhibited.

As a result, as illustrated in FIG. 4, it was confirmed that the cell percentage of the G1 phase, which is a division preparation phase, decreased and the cell percentage of the S phase, which is a division phase, increased in MCR-7 cells (STK32C) in which the STK32C gene was overexpressed, as compared to the control (see FIG. 4a), whereas the G1 phase cell percentage increased and the S phase cell percentage decreased in MDA-MB-231 cells (siSTK32C) and SK-BR-3 cells (siSTK32C), in which the expression of the STK32C gene was inhibited (see FIGS. 4b and 4c).

In addition, changes in the expression of cell cycle-related proteins in MCF-7 cells in which the STK32C gene was overexpressed and MDA-MB-231 cells in which the expression of the STK32C gene was inhibited were examined through western blotting. As controls, MCF-7 cells and MDA-MB-231 cells, prior to the overexpression or inhibition of the STK32C gene, were used.

Figure 5:
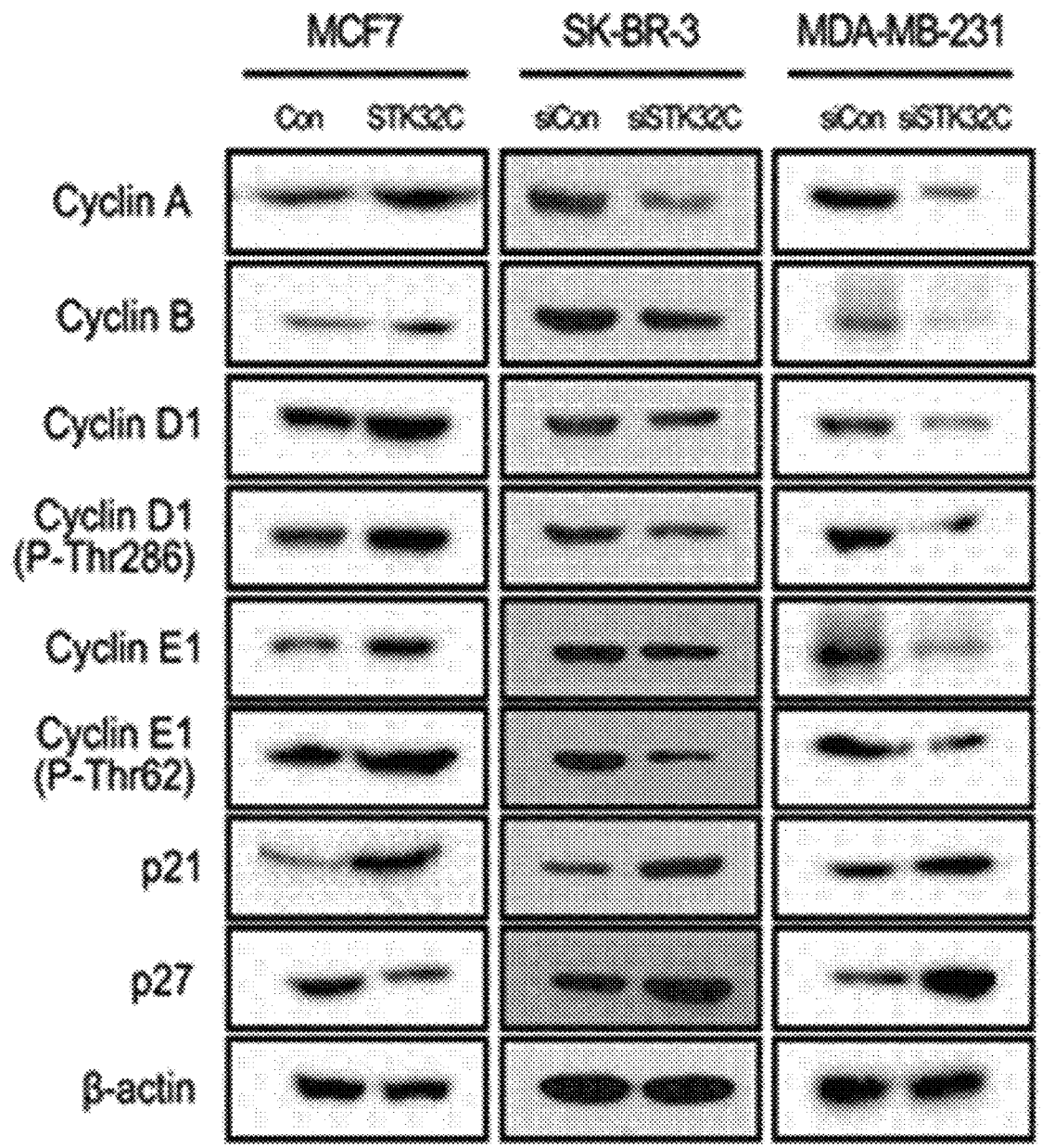
FIG. 5 illustrates verification results of changes in the expression of cell cycle-related proteins according to STK32 gene expression differences, wherein the expression was carried out in MCF-7 cells (STK32C) in which the STK32C gene was overexpressed, and MDA-MB-231 and SK-BR-3 cells in which the expression of the STK32C gene was inhibited.

As a result, as illustrated in FIG. 5, it was confirmed that the expressions of cyclin proteins, which are factors related to the progression of the cell cycle, increased and the expressions of p21 and p27 proteins, which inhibit the progression of the cell cycle, decreased in MCF-7 cells (STK32C) in which the STK32C gene was overexpressed, whereas the expressions of the cyclin proteins decreased and the expressions of the p21 and p27 proteins increased in MDA-MB-231 cells (siSTK32C) in which the expression of the STK32C gene was inhibited.

Taken together, the above results indicate that the progression of the cell cycle closely related to the division of breast cancer cells can be accelerated by overexpression of the STK32C gene, and can be inhibited by the inhibition of STK32C gene expression.

Example 2-3. Verification of Effect on Colony Formation of Breast Cancer Cells

A MCF-7 cell line in which the STK32C gene was overexpressed and a MDA-MB-231 cell line in which the expression of the STK32C gene was inhibited were cultured in a soft agarose medium, and then colony formation was examined through a microscope, and the number of colonies of each case was quantified for comparison. As controls, MCF-7 cells and MDA-MB-231 cells, prior to the overexpression or inhibition of the STK32C gene, were used.

Figure 6A:
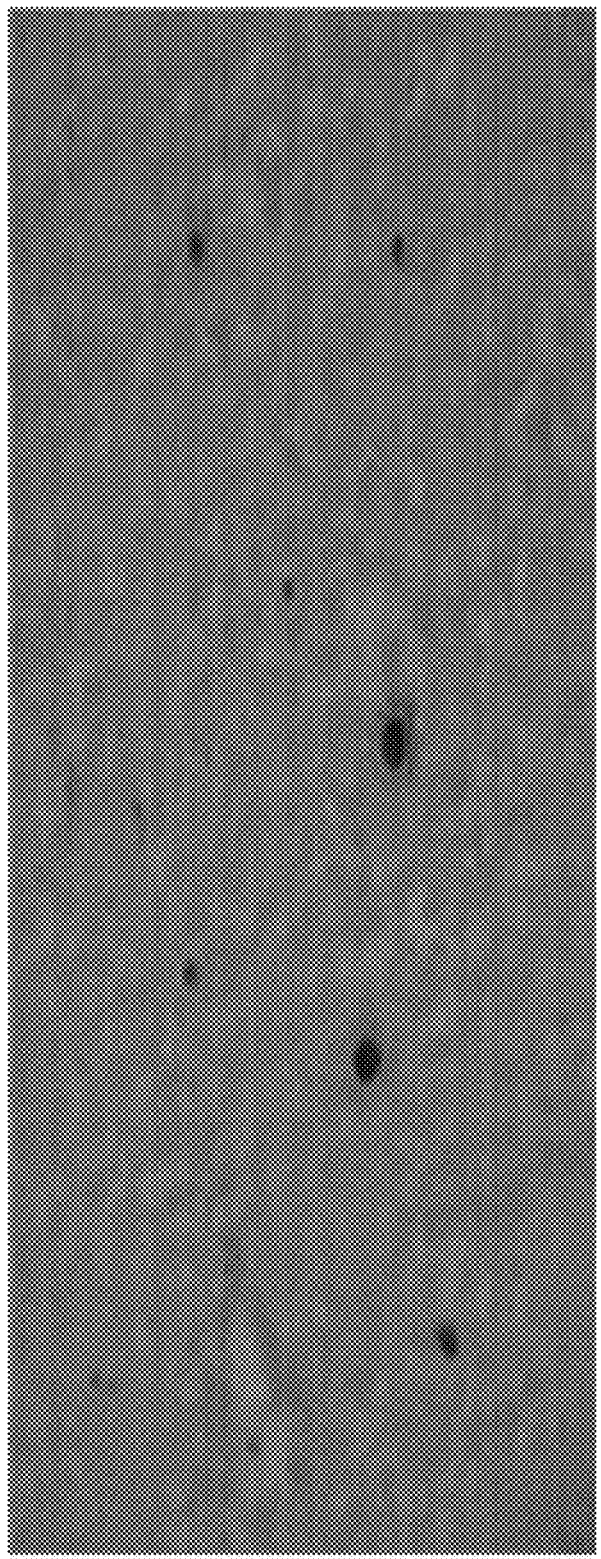
FIG. 6a illustrates a microscope observation result showing colony formation of MCF-7 cells in which the STK32C gene was not overexpressed.
Figure 6B:
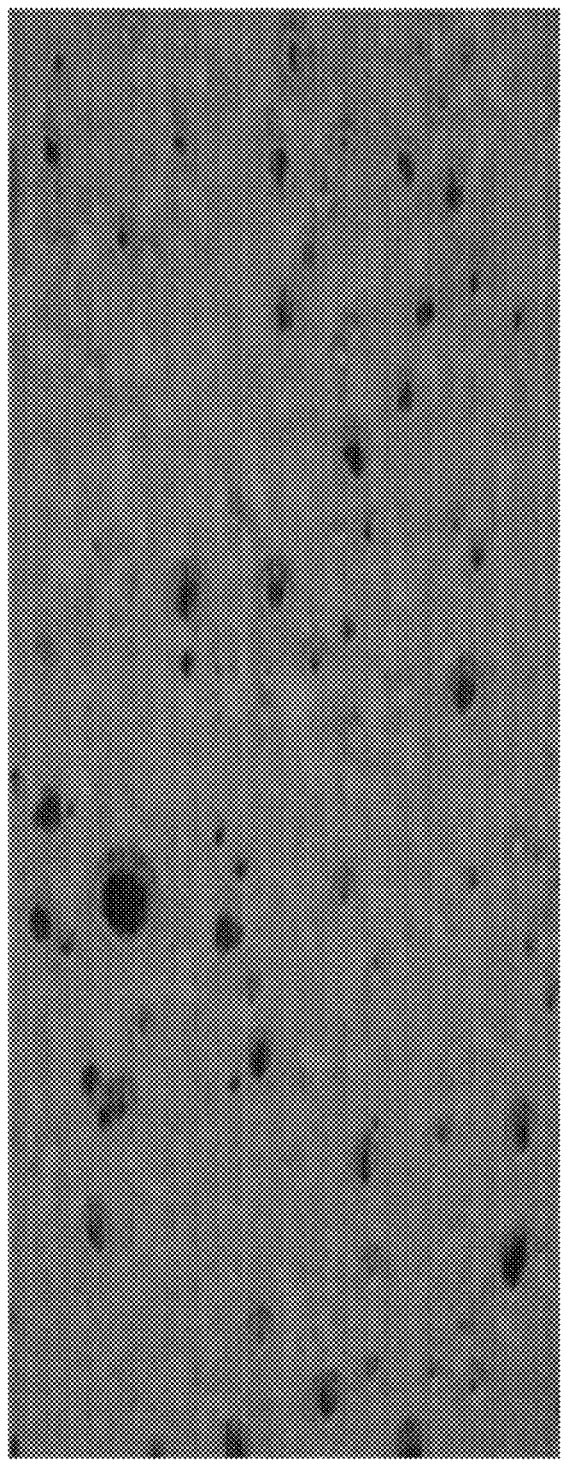
FIG. 6b illustrates a microscope observation result showing colony formation of MCF-7 cells in which the STK32C gene was overexpressed.
Figure 8A:
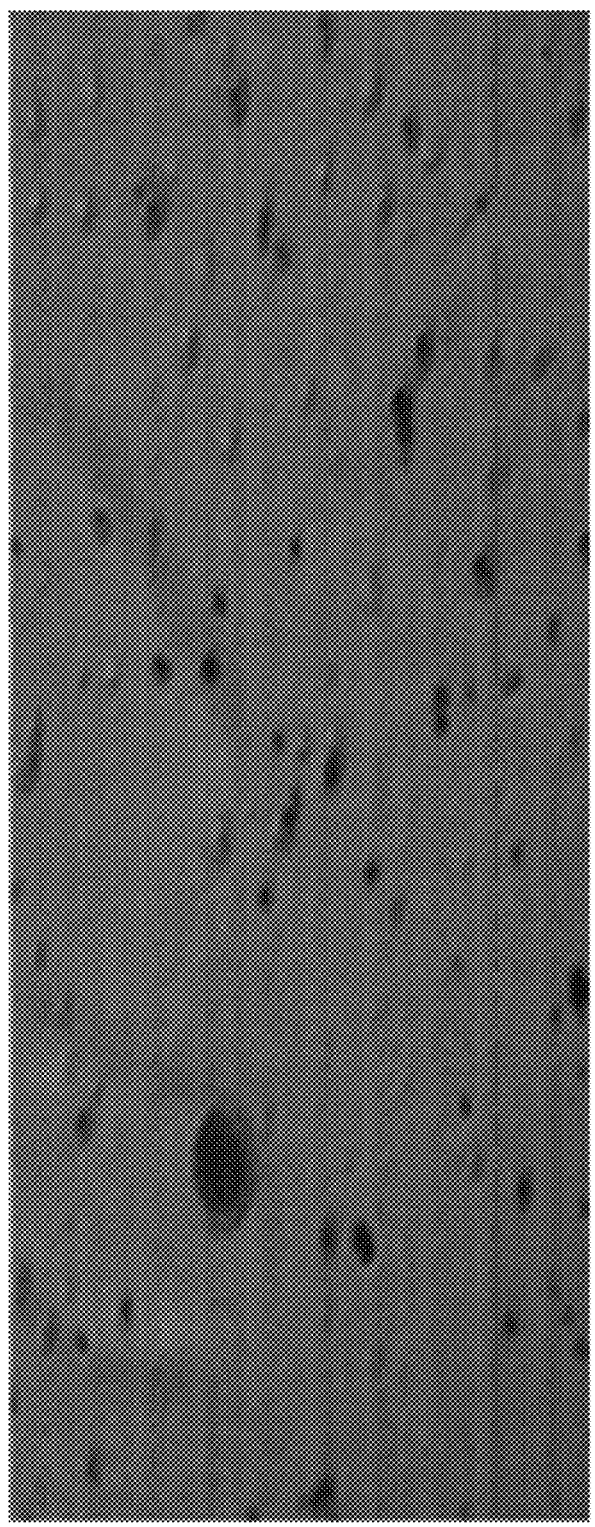
FIG. 8a illustrates a microscope observation result showing colony formation of MDA-MB-231 cells in which the expression of the STK32C gene was not inhibited.
Figure 8B:
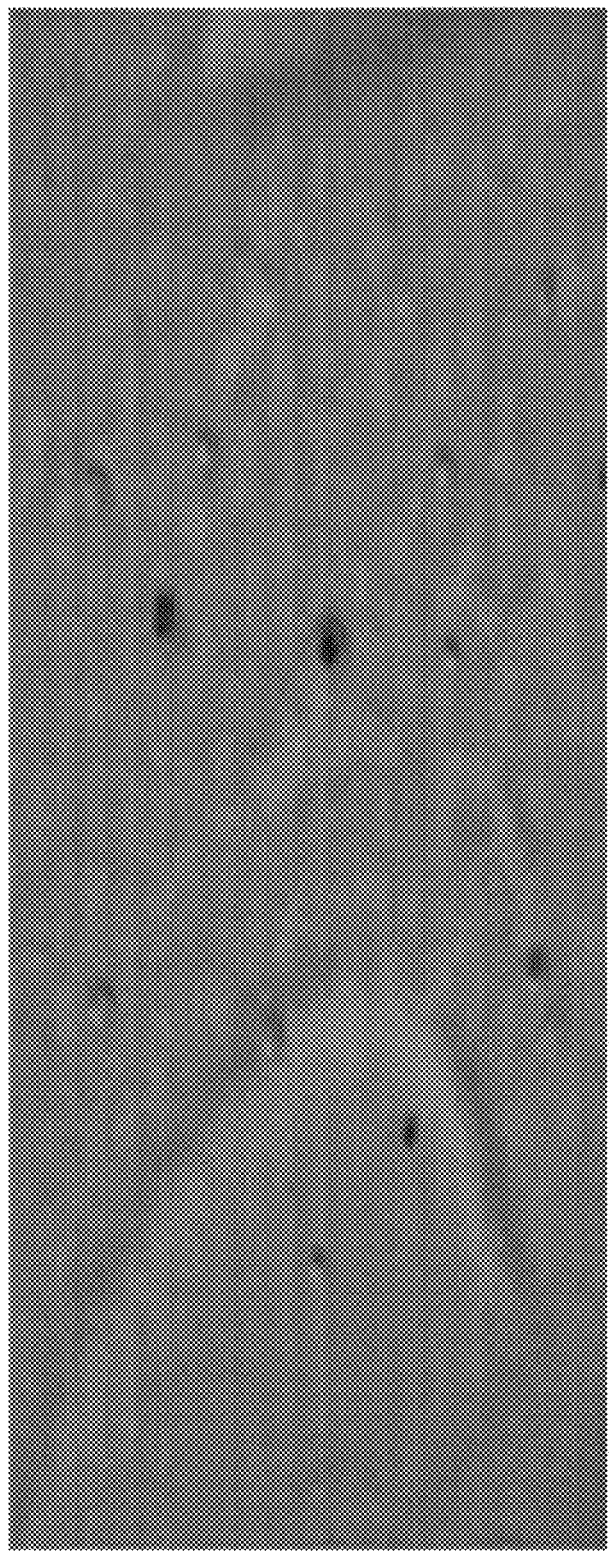
FIG. 8b illustrates a microscope observation result showing colony formation of MDA-MB-231 cells in which the expression of the STK32C gene was inhibited.

As a result, as illustrated in FIGS. 6 and 7, it was confirmed that the formation of colonies significantly increased in the MCF-7 cell line in which the STK32C gene was overexpressed, as compared to the control (see FIGS. 6a and 6b), and relatively increased about 5-fold (see FIG. 7). In contrast, as illustrated in FIGS. 8 and 9, it was confirmed that the formation of colonies significantly decreased in the MDA-MB-231 cell line in which the expression of the STK32C gene was inhibited (see FIGS. 8a and 8b) and relatively decreased about 6-fold (see FIG. 9), as compared to the control.

Taken together, the above results indicate that the colony formation of breast cancer cells is accelerated by the overexpression of the STK32C gene and is inhibited by the inhibition of STK32C gene expression.

Example 2-4. Verification of Effect on Metastasis of Breast Cancer Cells

In the case of metastatic breast cancer, cancer metastasis is accelerated by activating the epithelial-mesenchymal transition (EMT), and thus, in the present example, effects on cancer metastasis through changes in EMT according to STK32C gene expression differences were examined. In particular, expression patterns of N-cadherin and vimentin, which are mesenchymal markers, and E-cadherin, which is an epithelial marker, in MCF-10A and MCF-7 cell lines in which the STK32C gene was overexpressed and a MDA-MB-231 cell line in which the expression of the STK32C gene was inhibited were examined through western blotting and RT-PCR. In addition, the expression patterns of the markers were re-examined through confocal microscopy. As controls, MCF-10A cells, MCF-7 cells, and MDA-MB-231 cells, prior to the overexpression or inhibition of the STK32C gene, were used.

Figure 10A:
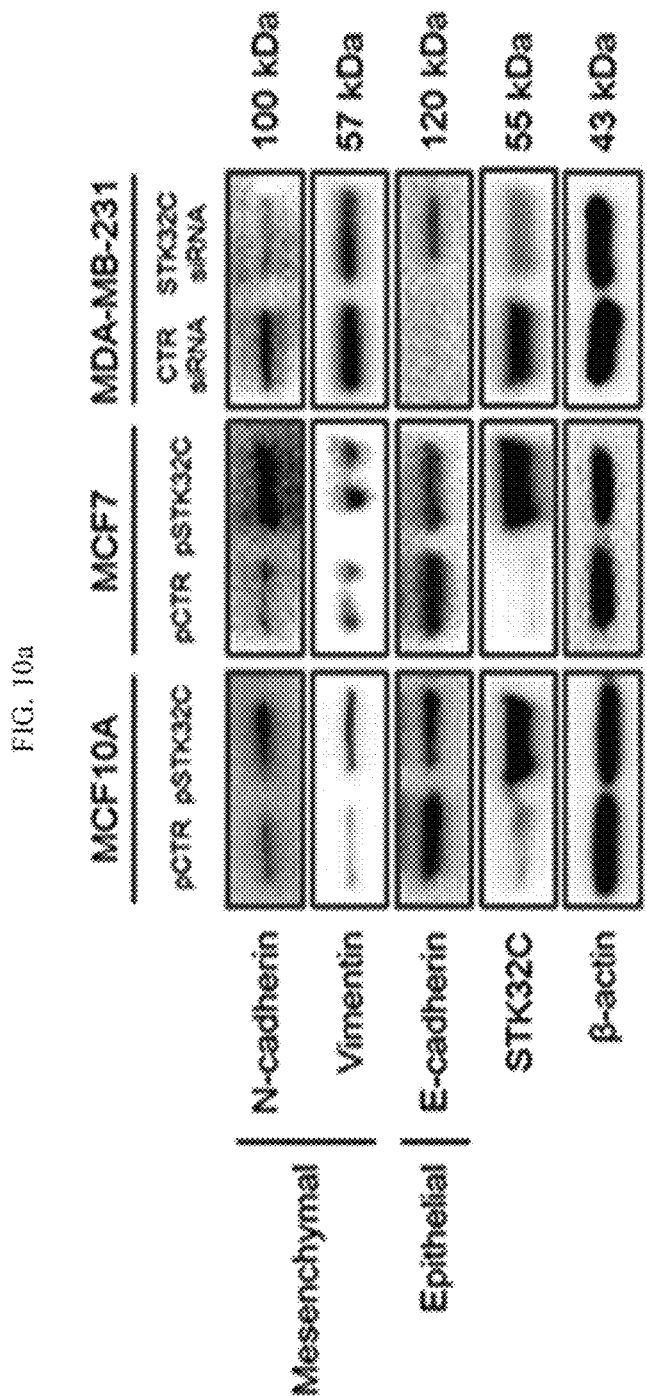
FIG. 10a illustrates western blotting results of the comparison between the expressions of N-cadherin, vimentin, and E-cadherin in MCF-10A cells, MCF-7 cells, and MDA-MB-231 cells.
Figure 10B:
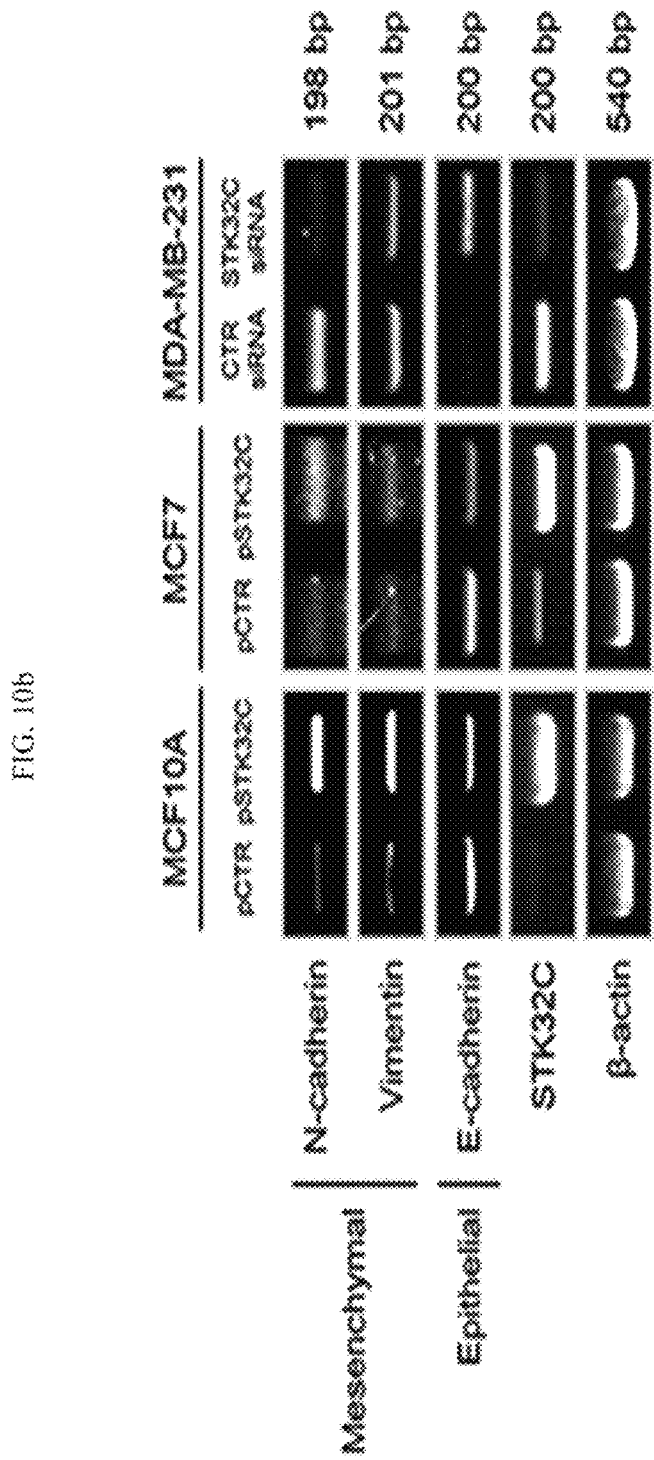
FIG. 10b illustrates RT-PCR results of the comparison between the expressions of N-cadherin, vimentin, and E-cadherin in MCF-10A cells, MCF-7 cells, and MDA-MB-231 cells.
Figure 11:
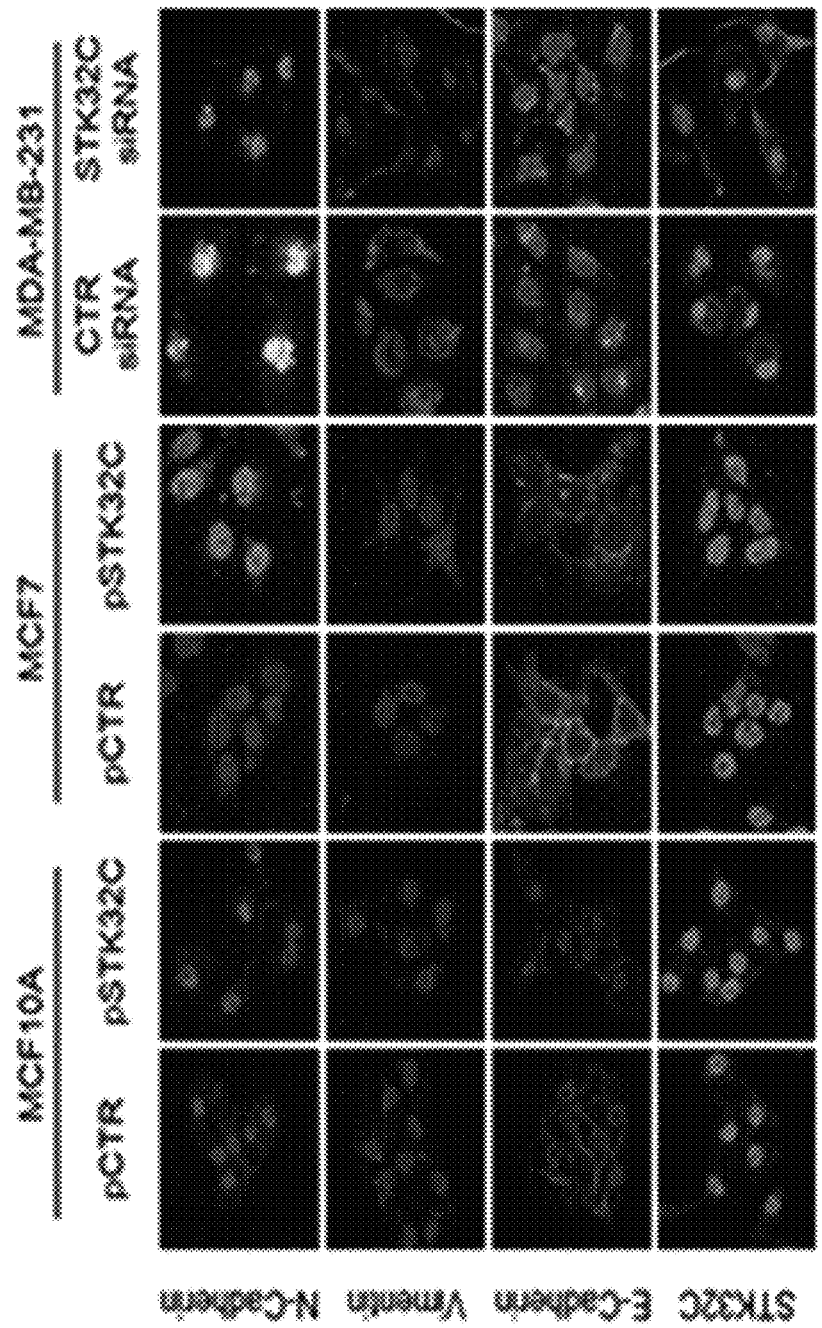
FIG. 11 illustrates confocal microscope verification results of the expressions of N-cadherin, vimentin, and E-cadherin in MCF-10A cells, MCF-7 cells, and MDA-MB-231 cells.

As a result, as illustrated in FIG. 10, it was confirmed through western blotting (see FIG. 10a) and RT-PCR (see FIG. 10b) that, in the MCF-10A and MCF-7 cells in which the STK32C gene was overexpressed, as compared to the controls, the expressions of N-cadherin and vimentin, which are mesenchymal markers, increased, while the expression of E-cadherin, which is an epithelial marker, decreased, and, in contrast to this, in the MDA-MB-231 cells in which the expression of the STK32C gene was inhibited, as compared to the control, the expressions of N-cadherin and vimentin decreased, while the expression of E-cadherin increased. In addition, as illustrated in FIG. 11, the same experimental results as the above results were verified through confocal microscopy as well.

Taken together, the above results indicate that the metastasis of breast cancer cells is accelerated by the overexpression of the STK32C gene, and is inhibited by the inhibition of STK32C gene expression.

Example 2-5. Verification of Effect on Invasiveness of Breast Cancer Cells

Changes in invasiveness of breast cancer cells according to STK32 gene expression were examined using MCF-10A cells in which the STK32C gene was overexpressed and MDA-MB-231 cells in which the expression of the STK32C gene was inhibited. In particular, the STK32C gene was overexpressed in the MCF-10A cells, whereas the STK32C gene was subjected to gene silencing in the MDA-MB-231 cells, and then invasiveness degrees of breast cancer cells were quantified for comparison. As controls, MCF-10A cells and MDA-MB-231 cells, prior to the overexpression or inhibition of the STK32C gene, were used.

Figure 12C:
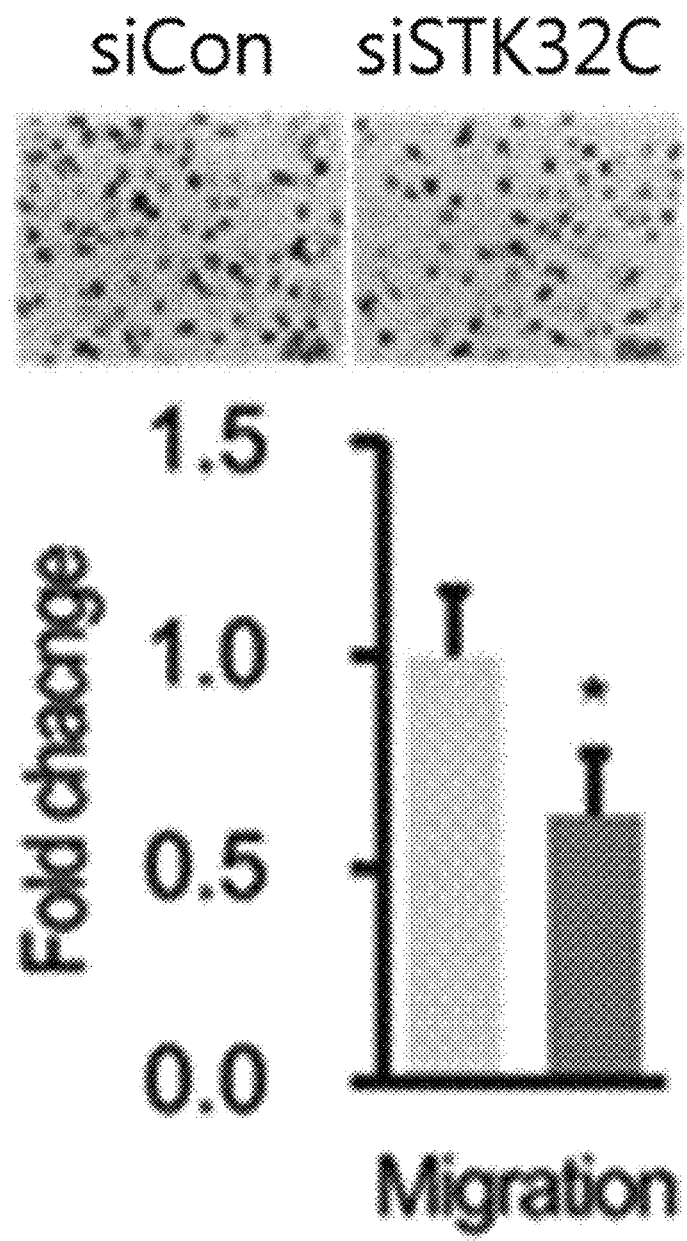
FIG. 12c illustrates verification results of the migration of cancer cells in SK-BR-3 cells (STK32C siRNA) in which the expression of the STK32C gene was inhibited.
Figure 13A:
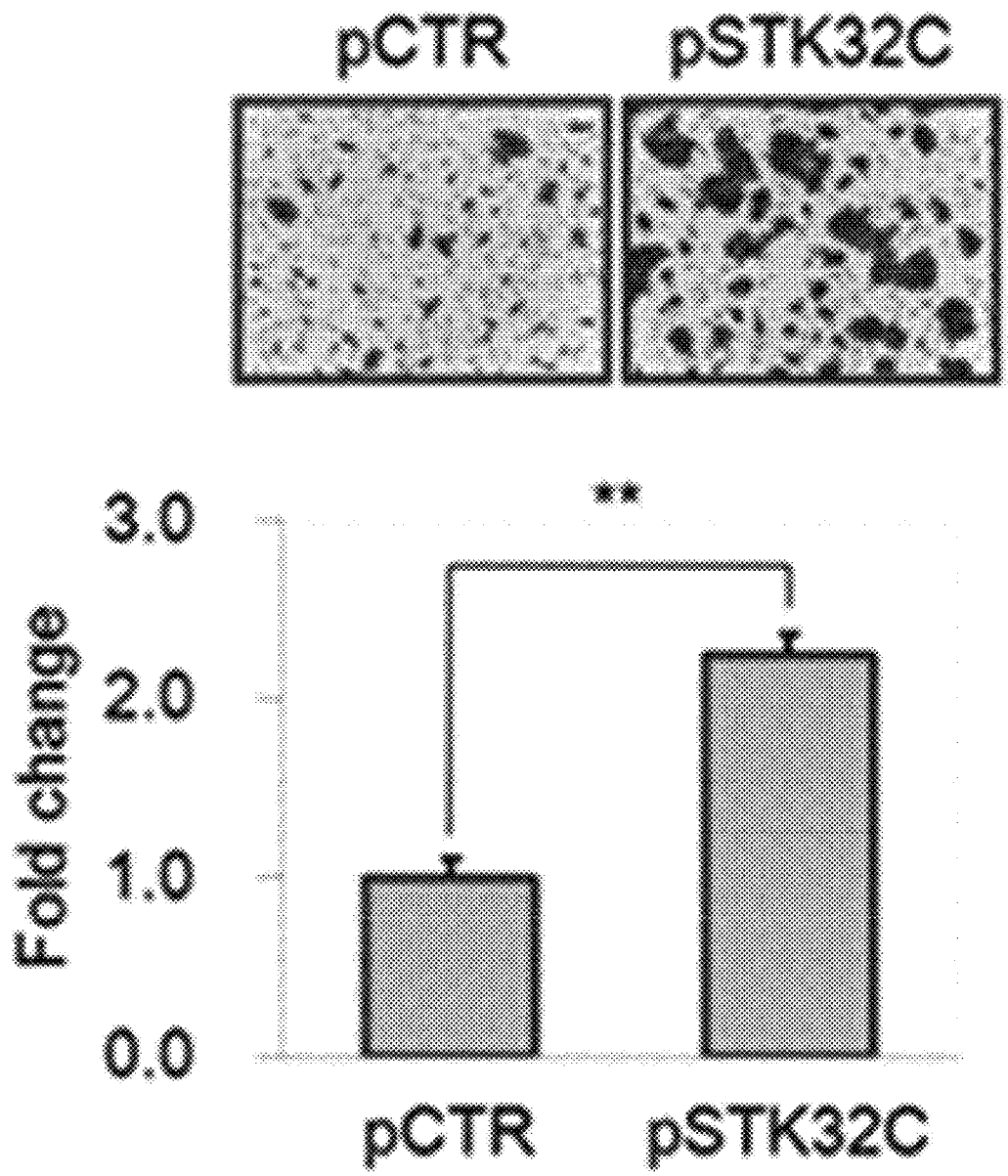
FIG. 13a illustrates verification results of the invasiveness of cancer cells in MCF-10 cells (pSTK32C) in which the STK32C gene was overexpressed.
Figure 13B:
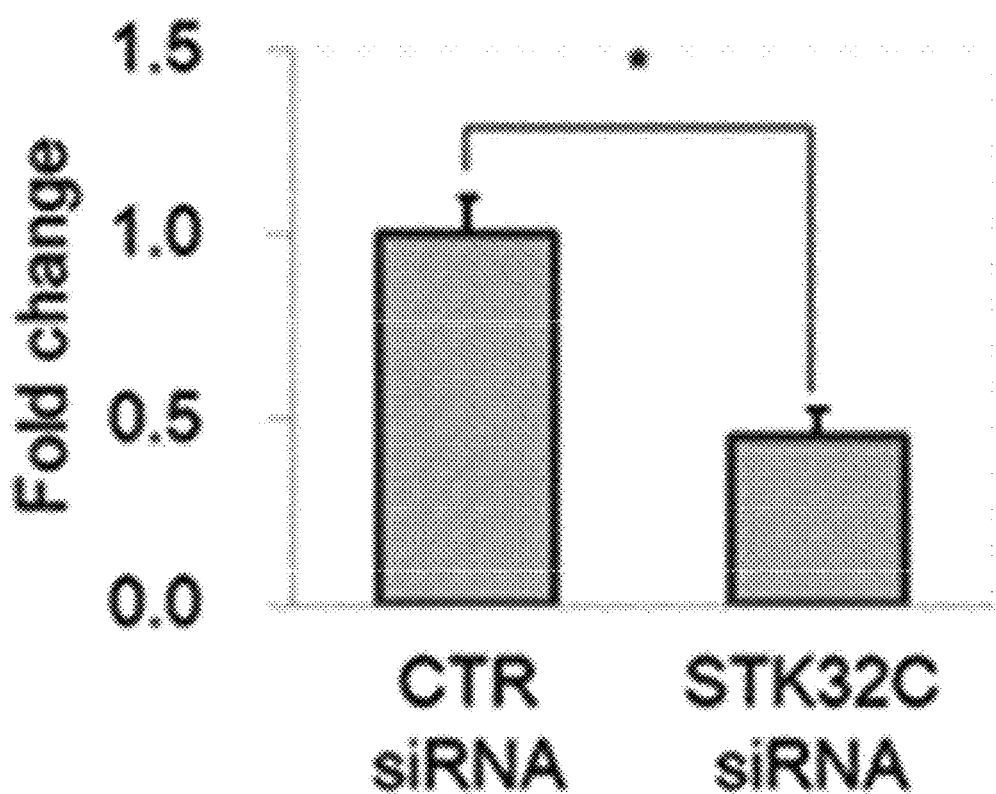
FIG. 13b illustrates verification results of the invasiveness of cancer cells in MDA-MB-231 cells (STK32C siRNA) in which the expression of the STK32C gene was inhibited.

As a result, as illustrated in FIGS. 12 and 13, it was confirmed that migration and invasiveness significantly increased about two-fold to about four-fold in MCF-10A (pSTK32C) in which the STK32C gene was overexpressed (see FIGS. 12a and 13a), whereas migration and invasiveness significantly decreased in a MDA-MB-231 cell line (STK32C siRNA) and SK-BR-3 cells (STK32CsiRNA), in which the expression of the STK32C gene was inhibited (see FIGS. 12b, 12c, 13b, and 13c).

Taken together, the above results indicate that the invasiveness of breast cancer cells is accelerated by overexpression of the STK32C gene, and is inhibited by the inhibition of STK32C gene expression.

Example 3. Verification of Breast Cancer Inhibitory Effect Using Mouse Animal Model In the present example, on the basis of experimental results of Example 2, a breast cancer inhibitory effect according to the inhibition of expression of the STK32C gene was examined using a mouse animal model. In particular, a MDA-MB-231-Luc/shSTK32C cell line, in which the expression of the STK32C gene was silenced in a MDA-MB-231 cell line containing luciferase, was cultured, and injected into mammary fads of SCID mice to induce breast cancer. Subsequently, changes in the volume of cancer cells were examined for 11 weeks, cancer tissues were extracted from the mice, and then changes in the volumes of the cancer tissues were visually observed, and changes in the expression of Ki67, which is a proliferation marker, were compared through immunochemical staining. As a control, a mouse animal model (MDA-MB-231-Luc/shCon), into which a MDA-MB-231 cell line in which the STK32C gene was not inhibited was injected, was used.

Figure 15A:
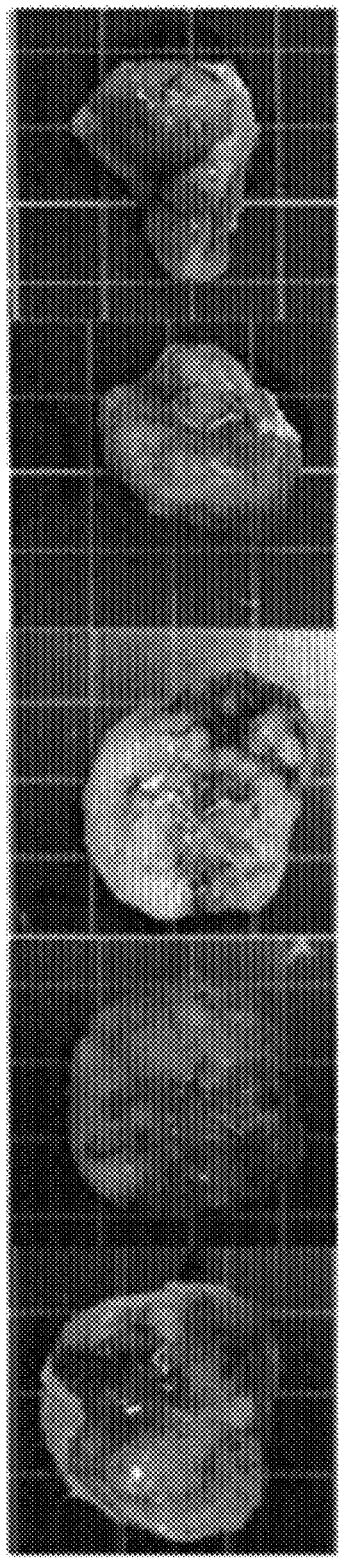
FIG. 15a illustrates visual observation results of changes in the volume of cancer tissue in a mouse animal model (MDA-MB-231-Luc/shCon) into which a MDA-MB-231 cell line, in which the STK32C gene was not inhibited, was injected.
Figure 16A:
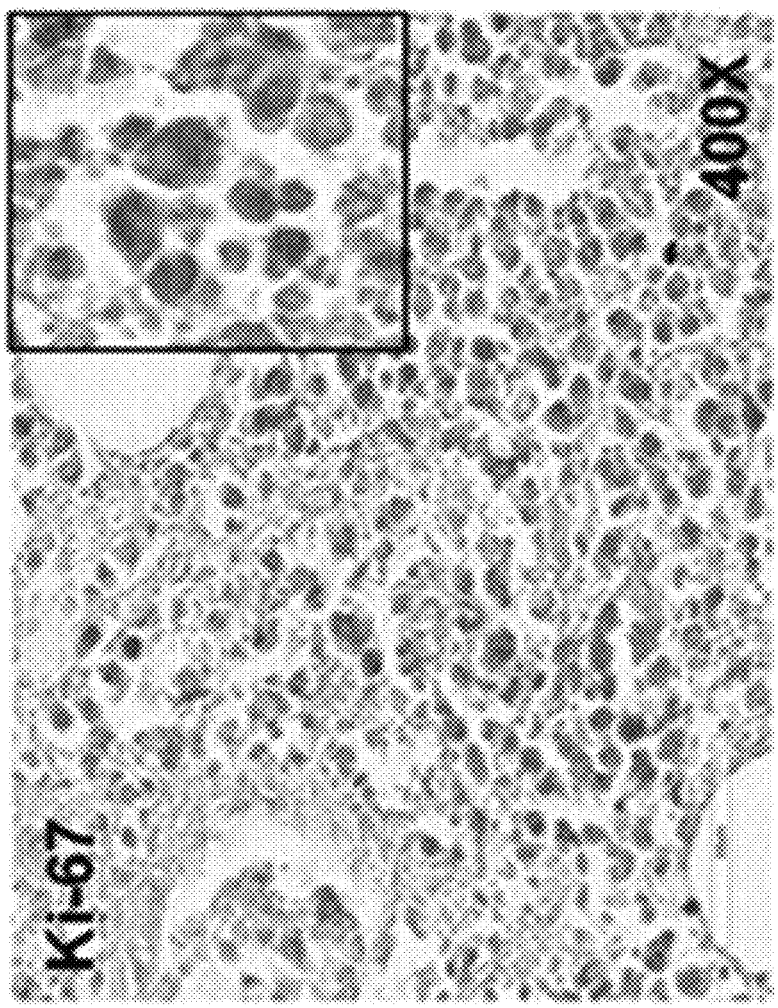
FIG. 16a illustrates a verification result of the expression of the proliferation marker Ki67 in a mouse animal model (MDA-MB-231-Luc/shCon) into which a MDA-MB-231 cell line, in which the STK32C gene was not inhibited, was injected.
Figure 16B:
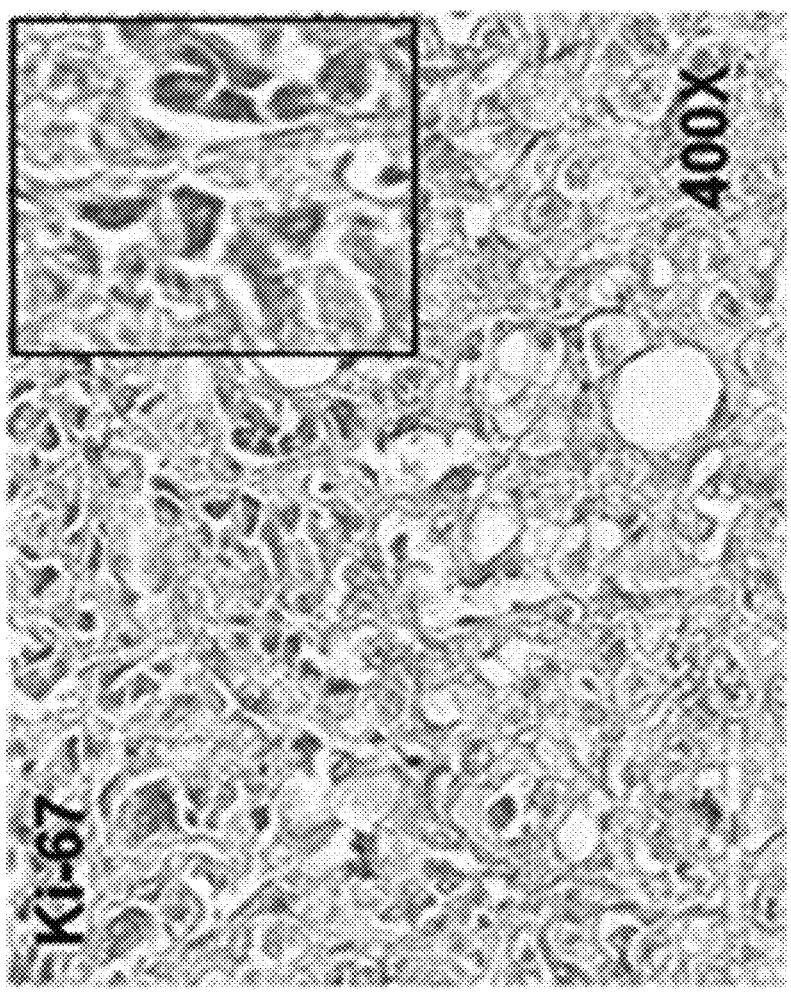
FIG. 16b illustrates a verification result of the expression of the proliferation marker Ki67 in a mouse animal model (MDA-MB-231-luc/shSTK32C) into which a MDA-MB-231 cell line, in which the expression of the STK32C gene was inhibited, was injected.

As a result, as illustrated in FIGS. 14 to 16, it was confirmed that, in mice (MDA-MB-231-Luc/shSTK32C) into which a MDA-MB-231 cell line, in which the expression of the STK32C gene was inhibited, was injected, as compared to the control, the volumes of cancer tissues significantly decreased over time (see FIGS. 14, 15a, and 15b), and the expression of Ki67, which is a proliferation marker, also decreased (see FIGS. 16a and 16b).

In addition, to verify metastasis to lung tissue, the activity of luciferase was examined using luciferin, and, after extraction of lung tissue, changes in invaded cells were compared through hematoxylin & eosin (H&E) staining. As a control, a mouse animal model (MDA-MB-231-Luc/shCon), into which a MDA-MB-231 cell line in which the STK32C gene was not inhibited was injected, was used.

Figure 17A:
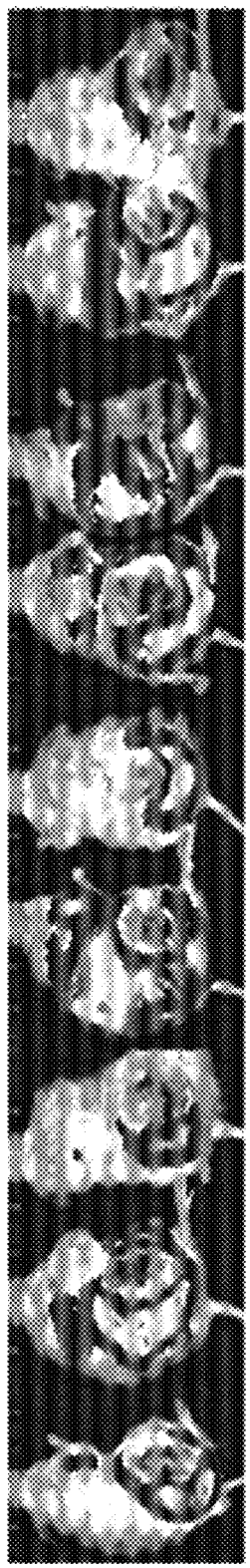
FIG. 17a illustrates verification results of metastasis to lung tissue through luciferase activity evaluation in a mouse animal model (MDA-MB-231-Luc/shCon) into which a MDA-MB-231 cell line, in which the STK32C gene was not inhibited, was injected.
Figure 17B:
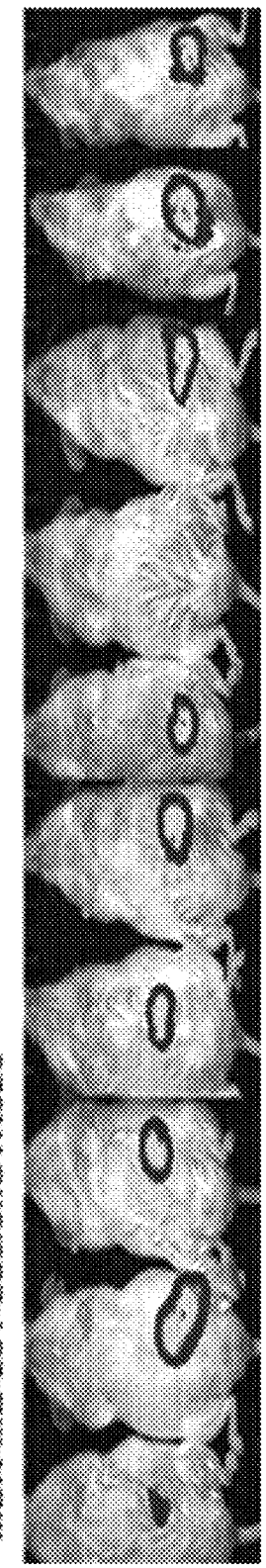
FIG. 17b illustrates verification results of metastasis to lung tissue through luciferase activity evaluation in a mouse animal model (MDA-MB-231-Luc/shSTK32C) into which a MDA-MB-231 cell line, in which the expression of the STK32C gene was inhibited, was injected.
Figure 18A:
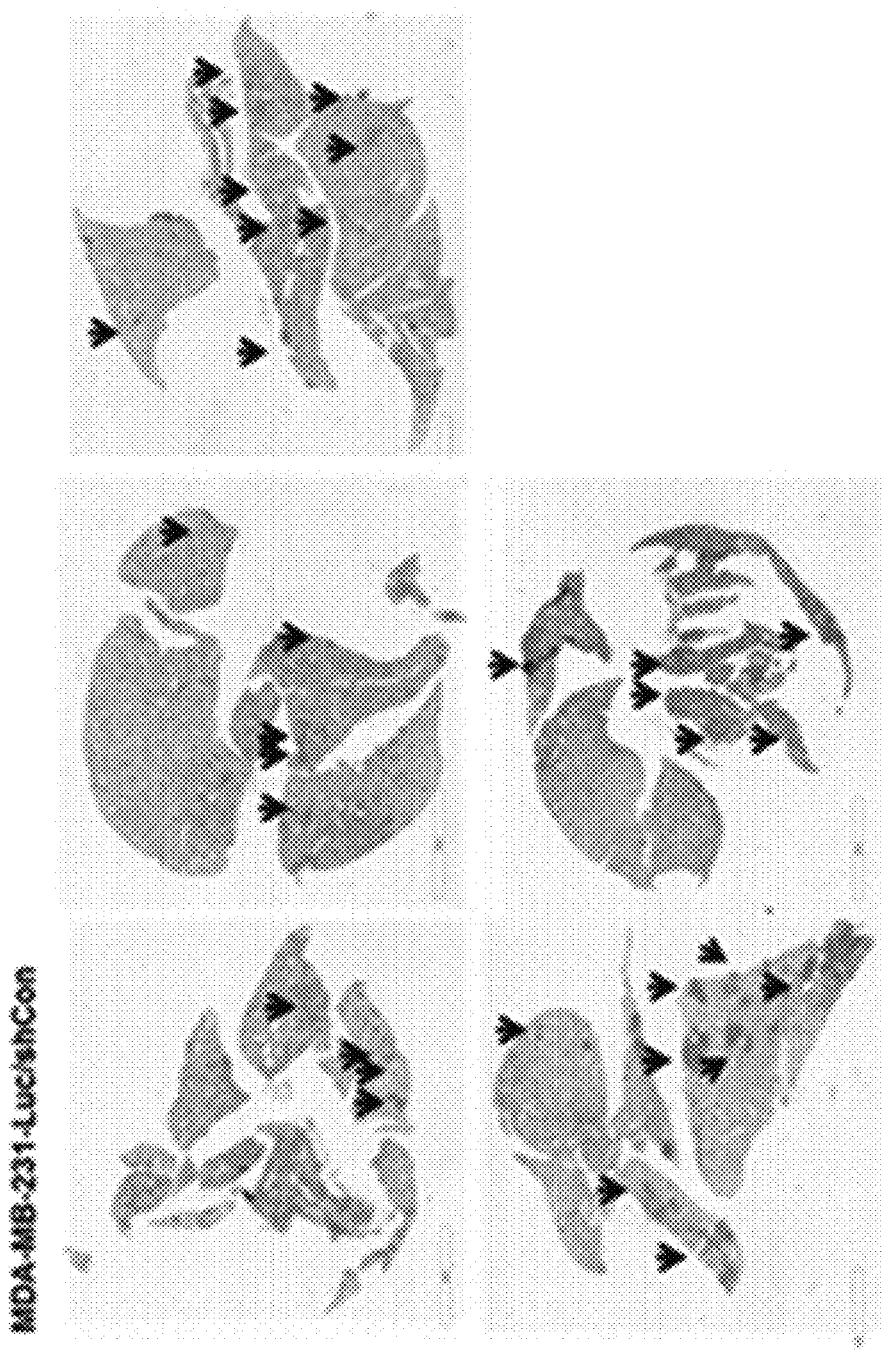
FIG. 18a illustrates verification results of metastasis to lung tissue through hematoxylin & eosin (H&E) staining in a mouse animal model (MDA-MB-231-Luc/shCon) into which a MDA-MB-231 cell line, in which the STK32C gene was not inhibited, was injected.
Figure 18B:
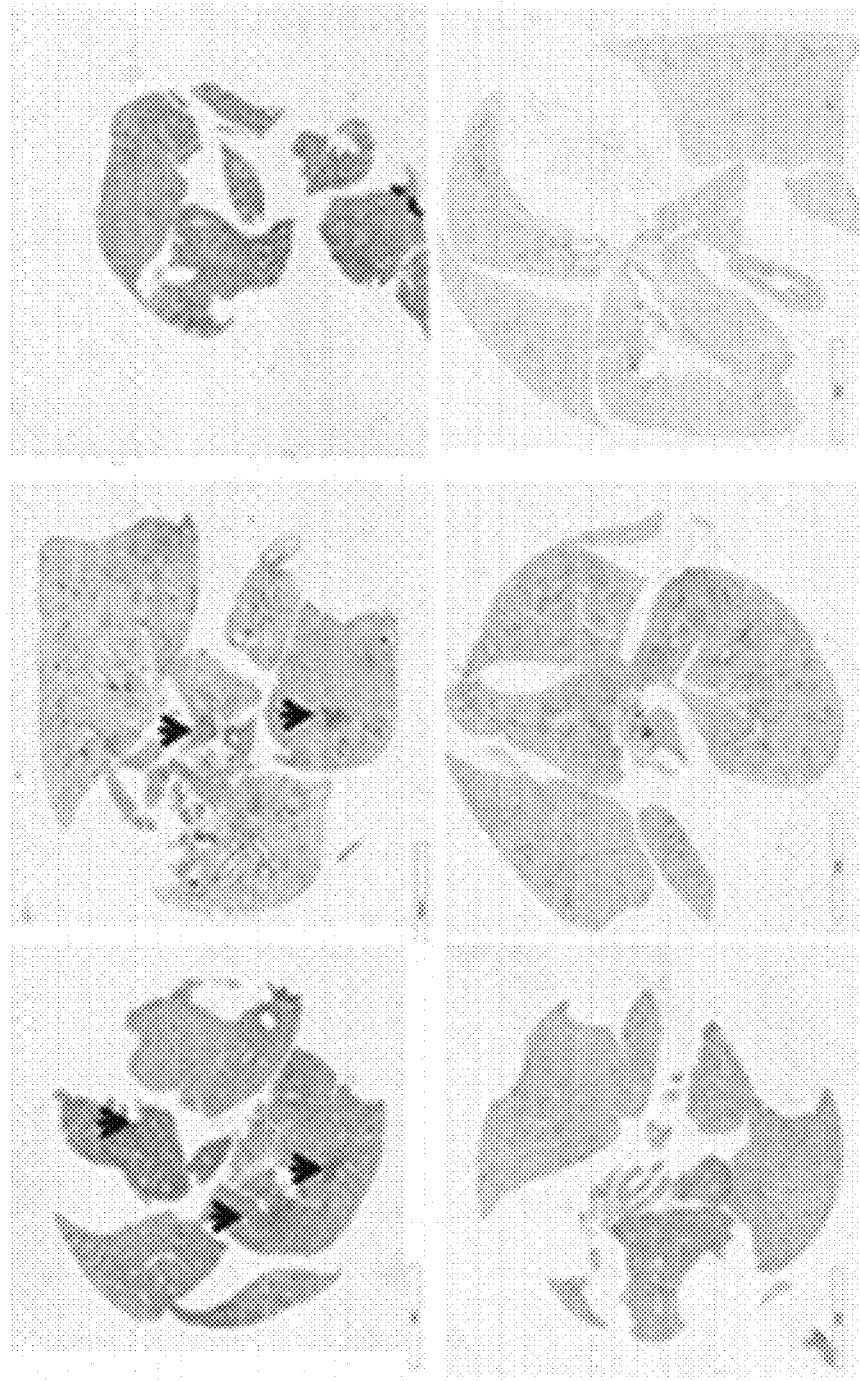
FIG. 18b illustrates verification results of metastasis to lung tissue through hematoxylin & eosin (H&E) staining in a mouse animal model (MDA-MB-231-luc/shSTK32C) into which a MDA-MB-231 cell line, in which the expression of the STK32C gene was inhibited, was injected.

As a result, as illustrated in FIG. 17, the activity of luciferase was systematically identified in the control (see FIG. 17a), whereas the activity of luciferase was locally observed in the mice (MDA-MB-231-Luc/shSTK32C) into which a MDA-MB-231 cell line, in which the expression of the STK32C gene was inhibited, was injected (see FIG. 17b). In addition, as illustrated in FIG. 18, it was confirmed through H&E staining as well that metastasis to lung tissue was progressed in the control (see FIG. 18a), whereas metastasis to lung tissue hardly occurred in the mice (MDA-MB-231-Luc/shSTK32C) into which a MDA-MB-231 cell line, in which the expression of the STK32C gene was inhibited, was injected (see FIG. 18b).

Taken together, the above results indicate that, similarly to the results of Example 2, the proliferation and metastasis of breast cancer cells may be inhibited by inhibiting the expression of the STK32C gene in vivo.

Example 4. Verification of Substrate Protein of STK32C

In the present example, a substrate protein of STK32C was discovered and a specific region of the substrate protein which was phosphorylated by the STK32 gene was identified. In particular, the substrate protein of STK32C was identified by immunoprecipitation, and the result was verified by re-immunoprecipitation using the detected substrate protein. In addition, specific regions (serine 165 and serine 167) of the substrate protein that were expected to be phosphorylated were subjected to site-directed mutagenesis into alanine, and then an in vitro kinase assay was performed using the modified substrate protein and STK32C as a substrate and an enzyme source, respectively, and, at this time, P32-labeled ATP was used.

Figure 19A:
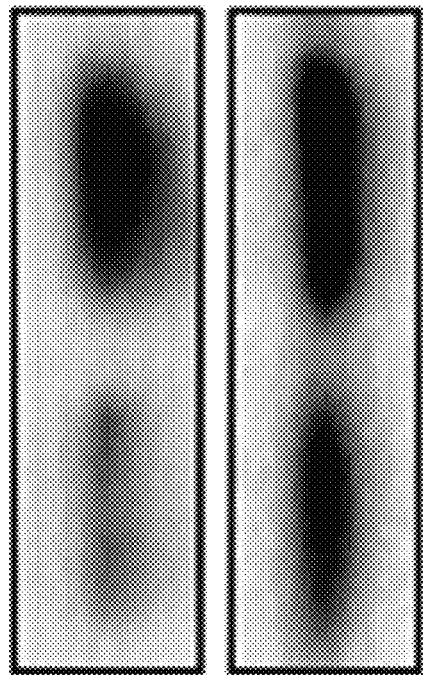
FIG. 19a illustrates results of immunoprecipitation using STK32C as an antibody to discover a substrate protein of STK32C.
Figure 19B:
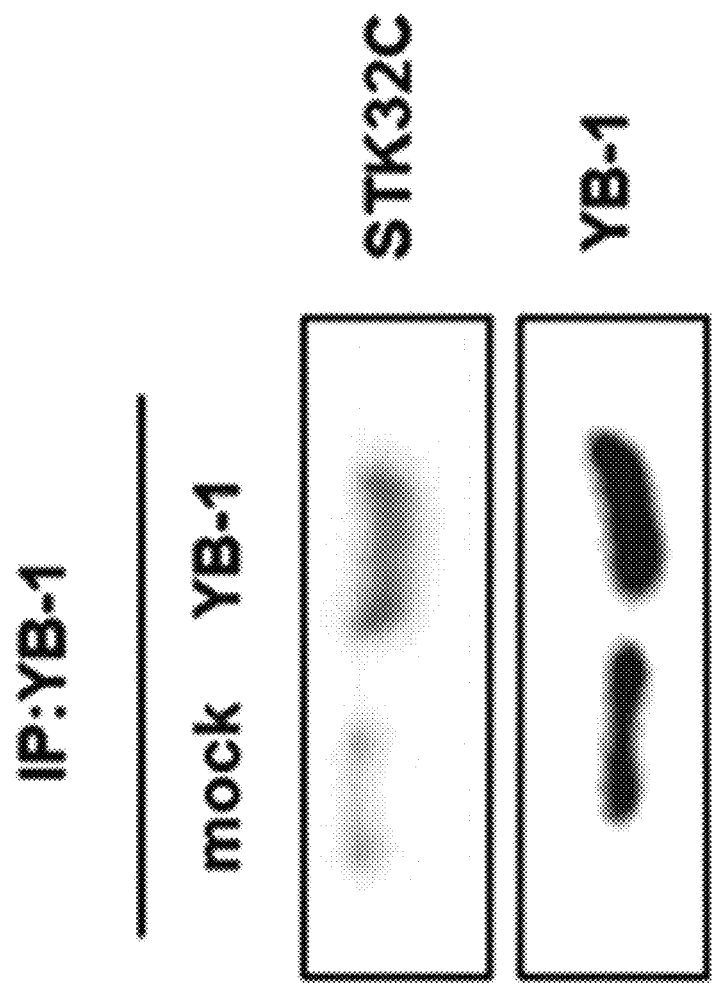
FIG. 19b illustrates results of immunoprecipitation using YB-1, which is a substrate protein, to verify the substrate protein of STK32C.
Figure 20:
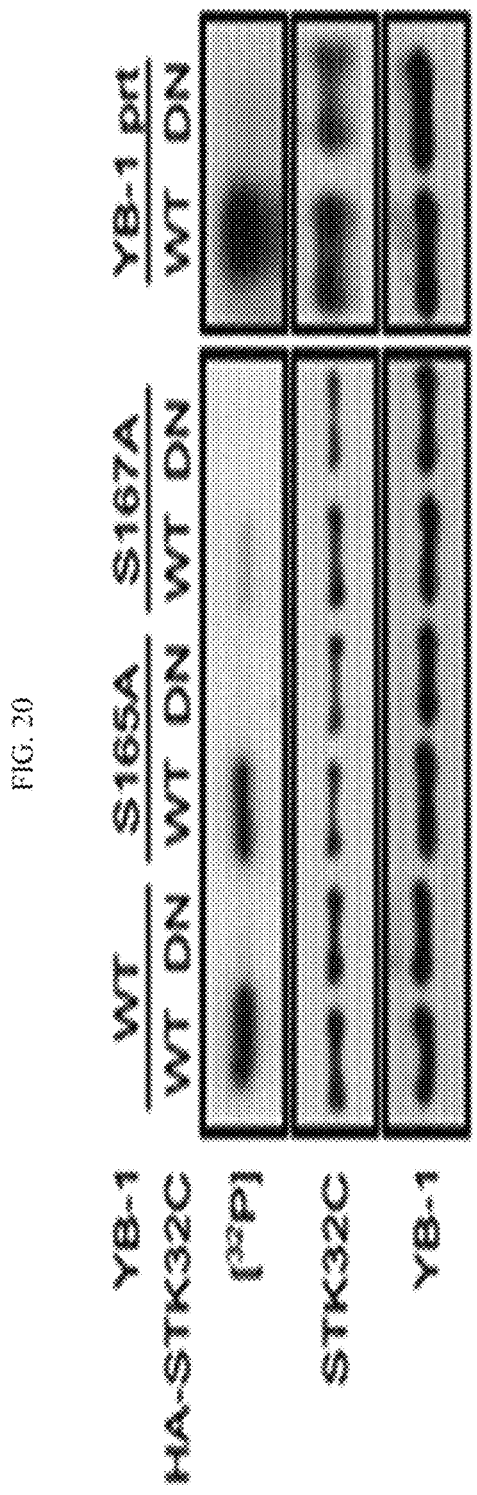
FIG. 20 illustrates in vitro kinase assay results obtained using YB-1 modified by STK32C and YB-1 modified by site-directed mutagenesis as an enzyme source and a substrate, respectively.

As a result, as illustrated in FIG. 19, the YB-1 protein was detected as the substrate protein of STK32C (see FIG. 19a), and the detection of SKT32C was identified as well in immunoprecipitation using YB-1, which verified the above result (see FIG. 19b). In addition, as illustrated in FIG. 20, it was confirmed that the serine 167 of the YB-1 substrate protein was phosphorylated by SKT32C.

Taken together, the above results indicate that the phosphorylation of the YB-1 substrate protein (serine 167) may be inhibited by the inhibition of SKT32C expression.

The foregoing description of the present invention is provided for illustrative purposes only, and it will be understood by those of ordinary skill in the art to which the present invention pertains that the present invention may be easily modified in other particular forms without changing the technical spirit or essential characteristics of the present invention. Thus, the embodiments described herein should be construed as being provided for illustrative purposes only and not for purposes of limitation.

INDUSTRIAL APPLICABILITY

The present invention relates to the serine threonine kinase 32C (STK32C) gene associated with breast cancer and a use thereof, a high expression level of the STK32C gene was verified in a variety of breast cancer cells or tissues, and changes in breast cancer cells according to STK32C gene expression differences were experimentally verified. In addition, a breast cancer inhibitory effect by the inhibition of expression of the STK32C gene and YB-1, which is a substrate protein, were newly identified, and thus the STK32C gene is expected to be used as a target gene for the diagnosis or treatment of breast cancer.

The invention claimed is:

1. A method of screening a breast cancer therapeutic material, the method comprising the following processes:
   a) treating serine threonine kinase 32C (STK32C)-expressing cells with a test material;
   b) measuring an expression or activity level of STK32C in the cells; and
   c) selecting a test material that inhibits expression or activity of STK32C when compared to a control not treated with the test material, as a breast cancer therapeutic material.

2. The method of claim 1, wherein the STK32C-expressing cells are selected from the group consisting of MCF-10A, MCF-7, MDA-MB-231, and SK-BR-3 breast cancer cells.

3. The method of claim 1, wherein the measuring of the expression or activity level of STK32C is performed by measuring a phosphorylation level of YB-1 by STK32C.

4. A method of diagnosing and treating a breast cancer, the method comprising the following processes:
   a) measuring an expression or activity level of serine threonine kinase 32C (STK32C) in a subject-derived biological sample using an agent that measures an expression or activity level of STK32C;
   b) diagnosing a case in which the measured expression or activity level of STK32C is higher than that of a normal control, as having breast cancer, and
   c) administering an expression or activity inhibitor of serine threonine kinase 32C (STK32C) to the subject.

5. A method of treating breast cancer, the method comprising administering an expression or activity inhibitor of serine threonine kinase 32C (STK32C) to a subject in need.

6. The method of claim 4, wherein the agent that measures an expression or activity level of STK32C comprises at least one selected from the group consisting of a primer, a probe, a protein, and an antibody that specifically bind to STK32C.

7. The method of claim 5, wherein the expression inhibitor of STK32C comprises at least one selected from the group consisting of an antisense oligonucleotide, siRNA, shRNA, microRNA, and a ribozyme that specifically bind to STK32C.

8. The method of claim 5, wherein the activity inhibitor of STK32C comprises at least one selected from the group consisting of a compound, a peptide, an aptamer, a protein, and an antibody that specifically bind to STK32C.

9. The method of claim 5, wherein the expression or activity inhibitor of STK32C inhibits the phosphorylation of YB-1.

* * * * *

SEQUENCE LISTING

```
<160> NUMBER OF SEQ ID NOS: 4

<210> SEQ ID NO 1
<211> LENGTH: 19
<212> TYPE: RNA
<213> ORGANISM: Artificial Sequence
<220> FEATURE:
<223> OTHER INFORMATION: sc-90587A_sense

<400> SEQUENCE: 1
gaugucaagc cugacaaca                                             19

<210> SEQ ID NO 2
<211> LENGTH: 19
<212> TYPE: RNA
<213> ORGANISM: Artificial Sequence
<220> FEATURE:
<223> OTHER INFORMATION: sc-90587A_antisense
```

```
<400> SEQUENCE: 2
uguugucagg cuugacauc                                              19

<210> SEQ ID NO 3
<211> LENGTH: 19
<212> TYPE: RNA
<213> ORGANISM: Artificial Sequence
<220> FEATURE:
<223> OTHER INFORMATION: sc-90587B_sense

<400> SEQUENCE: 3
ccgagaauga cuaucuuca                                              19

<210> SEQ ID NO 4
<211> LENGTH: 19
<212> TYPE: RNA
<213> ORGANISM: Artificial Sequence
<220> FEATURE:
<223> OTHER INFORMATION: sc-90587B_antisense

<400> SEQUENCE: 4
ugaagauagu cauucucgg                                              19
```